United States Patent [19]
Rinaldi et al.

[11] Patent Number: 6,013,648
[45] Date of Patent: Jan. 11, 2000

[54] CB$_2$ RECEPTOR AGONIST COMPOUNDS

[75] Inventors: Murielle Rinaldi, Saint Georges d'Orques; Francis Barth; Pierre Casellas, both of Montpellier; Christian Congy, Saint Gely du Fesc; Didier Oustric, Le Cres, all of France; Malcolm R. Bell, East Greenbusch; Thomas E. D'Ambra, Rexford, both of N.Y.; Richard E. Philion, Pottstown, Pa.

[73] Assignee: Sanofi, Paris, France

[21] Appl. No.: 08/995,902

[22] Filed: Dec. 22, 1997

Related U.S. Application Data

[63] Continuation of application No. PCT/FR96/00959, Jun. 20, 1996.

[30] Foreign Application Priority Data

Jun. 21, 1995 [FR] France ................................. 95 07438

[51] Int. Cl.[7] ...................... A61K 31/405; A61K 31/535; C07D 209/12; C07D 413/06
[52] U.S. Cl. .................................. 514/235.2; 514/228.2; 514/323; 514/414; 514/419; 544/58.5; 544/143; 544/144; 546/201; 548/465; 548/468; 548/493
[58] Field of Search .................................. 548/468, 493, 548/465; 514/414, 419, 228.2, 235.2, 323; 544/58.5, 143, 144; 546/201

[56] References Cited

U.S. PATENT DOCUMENTS

| | | | |
|---|---|---|---|
| 4,973,587 | 11/1990 | Ward et al. | 514/235.2 |
| 5,013,837 | 5/1991 | Ward et al. | 544/143 |
| 5,081,122 | 1/1992 | Ward | 514/235.7 |

FOREIGN PATENT DOCUMENTS

| | | | |
|---|---|---|---|
| 0 444 451 A2 | 9/1991 | European Pat. Off. | |
| WO97 00860 | 1/1997 | WIPO. | |

OTHER PUBLICATIONS

Kaminski, Adv. Exp. Med. Biol.,335:115–120 (1993).
D'Ambra et al., Journal of Medicinal Chemistry, 35:124–135 (1992).
Chemical Abstracts, vol. 99, No. 25, Dec. 19, 1983 (Sarbu et al., Descrierea Inventiei 77049).
Chemical Abstract, vol. 107, No. 15, Oct. 12, 1987 (Sarbu et al. Descrierea Inventiei 90049).
Sarbu et al., Rev. Roum. Chim., 25: 245–251 (1980).
Huffman et al., Bioorg. Med. Chem. Lett., 4: 563–566 (1994).
Bell et al., J. Med. Chem., 34: 1110–1116 (1991).
Pacheco et al., J. Pharmacol. Exp. Ther., 257: 170–183 (1991).
Chemical Abstracts, vol. 124, No. 17, 1425 (1996) (D'Ambra et al., Bioorg. Med. Chem. Lett., 6.
Chemical Abstracts, vol. 123, No. 3, 59–60 (1995) (Pertwee et al., Life Sci., 56: 23/24 (1995)).
Yamada et al., J. Med. Chem., 39: 1967–1974 (1996).
Eissenstat et al., J. Med Chem., 38: 3094–3105 (1995).
Derocq et al., Febs Letters, 369: 177–182 (1995).

Primary Examiner—Richard L. Raymond
Attorney, Agent, or Firm—Bacon & Thomas PLLC

[57] ABSTRACT

The use of human CB$_2$ receptor-specific agonists of formula (I) or (I') for preparing immunomodulating drugs is disclosed. In formulae (I) and (I'), $R_1$ is a group selected from —$CH_2CHR_{10}NR_6R_{11}$, —$(CH_2)_2NR'_6R'_{11}$, —$CHR_9CH_2NR'_6R'_{11}$, —$(CH_2)_nZ$ and —$COR_8$; $R'_1$ is a —$CH_2CHR_{10}NR_6R_{11}$ or —$(CH_2)_2NR'_6R'_{11}$ group; $R_2$ and $R'_2$ are hydrogen, halogen or $C_{1-4}$ alkyl; $R_3$ is hydrogen, $C_{1-4}$ alkyl or a group selected from —$CH_2CHR_{10}NR_6R_{11}$, —$(CH_2)_2NR'_6R'_{11}$ and —$COR_8$; $R'_3$ is a =$CR_6R_8$ group; $R_4$ has one of the meanings given for $R_5$ or is a —$COR_8$ group; $R_5$ is hydrogen, $C_{1-4}$ alkyl, $C_{1-4}$ alkoxy, a halogen atom, a $CF_3$ group, an $OCF_3$ group or $C_{1-4}$ alkylthio; $R'_5$ has one of the meanings given for $R_5$ and is in the 5 or 6 position of the indene ring; $R_6$ is hydrogen or $C_{1-4}$ alkyl; $R'_6$ is $C_{1-4}$ alkyl; $R_7$ has one of the meanings given for $R_5$ or $R_7$ and $R_9$ together form a —Y—$CH_2$— group attached to the indole ring in the 7 position by a group Y; $R_8$ is phenyl substituted one to four times by a substituent selected from halogen, $C_{1-4}$ alkyl or $C_{1-4}$ alkoxy; a polycyclic ring selected from naphth-1-yl, naphth-2-yl, 1,2,3,4-tetrahydronaphth-1-yl, 1,2,3,4-tetrahydronaphth-5-yl, anthryl, benzofuryl, benzothien-2-yl, benzothien-3-yl, 2-, 3-, 4- or 8-quinolyl, said polycyclic rings optionally being substituted once or twice by a substituent selected from $C_{1-4}$ alkyl, $C_{1-4}$ alkoxy, $C_{1-4}$ alkylthio, halogen, cyano, hydroxyl, trifluoromethyl and imidazol-1-yl; $R_{10}$ and $R_{11}$ together are a group selected from —$CH_2$—O—$CH_2$—$CR_{12}R_{13}$— and —$(CH_2)_p$—$CR_{12}R_{13}$—, wherein the carbon atom substituted by $R_{12}$ and $R_{13}$ is attached to the nitrogen atom; $R'_{11}$ is $C_{1-4}$ alkyl; or $R'_{11}$ and $R'_6$, taken together with the nitrogen atom to which they are attached, form a group selected from morpholin-4-yl, thiomorpholin-4-yl, piperidin-1-yl and pyrrolidin-1-yl; each of $R_{12}$ and $R_{13}$ is independently hydrogen or $C_{1-4}$ alkyl; n is 2, 3, 4 or 5; p is 2 or 3; Z is a methyl group or a halogen atom; and Y is a methylene group or an oxygen atom.

8 Claims, No Drawings

CB₂ RECEPTOR AGONIST COMPOUNDS

The present application is a continuation of International Application No. PCT/FR96/00959, filed Jun. 20, 1996.

The present invention relates to the use of selective human $CB_2$ receptor agonists for the preparation of immunomodulating drugs. The invention further relates to novel human $CB_2$ receptor agonists and the pharmaceutical compositions in which they are present, and to the methods for their preparation.

$\Delta^9$-THC is the main active constituent extracted from *Cannabis sativa* (Tuner, 1985; in Marijuana 1984, Ed. Harvey, DY, IRL Press, Oxford). Numerous articles have described not only psychotropic effects of cannabinoids but also their influence on the immune function [HOLLISTER L. E., J. Psychoact. Drugs 24 (1992) 159–164]. The majority of in vitro studies have shown that cannabinoids have immunosuppressant effects: inhibition of the mitogen induced proliferative responses of T lymphocytes and B lymphocytes [Luo, Y. D. et al., Int. J. Immunopharmacol. (1992) 14, 49–56; Schwartz, H. et at., J. Neuroimmunol. (1994) 55, 107–115], inhibition of the activity of cytotoxic T cells [Klein et at., J. Toxicol. Environ. Health (1991) 32, 465–477], inhibition of the microbicidal activity of macrophages and of TNFα synthesis [Arata, S. et at., Life Sci. (1991) 49, 473–479; Fisher-Stenger et al., J. Pharm. Exp. Ther. (1993) 267, 1558–1565] and inhibition of the cytolytic activity and the TNFα production of large granular lymphocytes [Kusher et al., Cell. Immun. (1994) 154, 99–108]. In some studies, amplification effects have been observed, namely an increase in the bioactivity of interleukin-1 by mouse fixed macrophages or differentiated macrophagic cell lines, due to enhanced levels of TNFα [Zhu et al., J. Pharm. Exp. Ther. (1994) 25 270, 1334–1339; Shivers, S. C. et al., Life Sci. (1994) 54, 1281–1289].

The effects of cannabinoids are due to an interaction with high affinity specific receptors present in the central nervous system (Devane et al., Molecular Pharmacology (1988) 34, 605–613) and peripheral nervous system (Nye et al., The Journal of Pharmacology and Experimental Therapeutics (1985) 234, 784–791; 30 Kaminski et al., Molecular Pharmacology (1992) 42, 736–742; Munro et at., Nature (1993) 365, 61–65).

The central effects are dependent on a first type of cannabinoid receptor ($CB_1$), which is present in the brain. Furthermore, Munro et al. [Nature (1993) 365, 61–65] have cloned a second cannabinoid receptor coupled to protein G, called $CB_2$, which is present only in the peripheral nervous system and more particularly on the cells of immune origin. The presence of $CB_2$ cannabinoid receptors on the lymphoid cells may explain the immunomodulation, referred to above, which is exerted by cannabinoid receptor agonists.

The cannabinoid receptor agonists known hitherto are mixed agonists, i.e. they act on both the central receptors ($CB_1$) and the peripheral receptors ($CB_2$). Consequently, if it is desired to treat the immune system with the known cannabinoid receptor agonists, there is always an appreciable side effect, namely the psychotropic effect.

The following patents describe non-selective agonists: EP 0 570 920, WO 94-12466, which describes anandamide, and U.S. Pat. No. 4,371,720, which describes CP 55940.

Furthermore, as the $CB_2$ receptor has only been known since 1993, the numerous patents relating to cannabinoid compounds give no indication of their selectivity. The following may be mentioned in particular among these patents: U.S. Pat. No. 5,081,122, U.S. Pat. No. 5,292,736, U.S. Pat. No. 5,013,387 and EP 0 444 451, which describe compounds with an indole or indene structure.

Other indole derivatives with cannabinoid activity are described in J. W. Hufman et al., Biorg. Med. Chem. Lett. (1994) 4, 563.

It has now been found that specific human $CB_2$ receptor agonists which have a high affinity for said receptor are potent immunomodulators which can be used without the risk of the side effect indicated above.

In the present description, "high affinity for the human $CB_2$ receptor" denotes an affinity characterized by an affinity constant which is less than or equal to 10 nM, and "specific" denotes the compounds whose affinity constant for the $CB_2$ receptor is at least 30 times less than the affinity constant for the $CB_1$ receptor and for which the affinity constant for the $CB_1$ receptor is greater than or equal to 100 nM. Moreover, the compounds of the invention also exhibit specificity towards other receptors; the compounds of the invention actually have an inhibition constant greater than 1 μM for human receptors other than the cannabinoid receptors.

Thus the present invention relates to the use of the specific human $CB_2$ receptor agonists for the preparation of immunomodulating drugs.

The compounds of formulae (I) and (I') below may be mentioned as examples of specific $CB_2$ receptor agonists which are suitable for the purposes of the invention.

The compounds which are suitable for the purposes of the invention are the compounds of formula (I) or (I') below in the form of pure enantiomers or in the form of racemates:

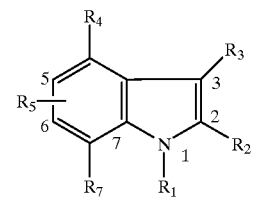

(I)

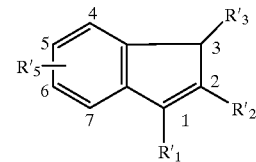

(I')

in which:

$R_1$ is a group selected from the groups —$CH_2CHR_{10}NR_6R_{11}$; —$(CH_2)_2NR'_6R'_{11}$; —$CHR_9CH_2NR'_6R'_{11}$; —$(CH_2)_nZ$ and —$COR_8$;

$R'_1$ is the group —$CH_2CHR_{10}NR_6R_{11}$ or the group —$(CH_2)_2NR'_6R'_{11}$;

$R_2$ and $R'_2$ are hydrogen, a halogen or a ($C_1$–$C_4$)alkyl;

$R_3$ is hydrogen, a ($C_1$–$C_4$)alkyl or a group selected from the groups —$CH_2CHR_{10}NR_6R_{11}$; —$(CH_2)_2NR'_6R'_{11}$ and —$COR_8$;

$R'_3$ is the group =$CR_6R_8$;

$R_4$ has one of the meanings given for $R_5$ or is a group —$COR_8$;

$R_5$ is hydrogen, a ($C_1$–$C_4$)alkyl, a ($C_1$–$C_4$)alkoxy, a halogen atom, a group —$CF_3$, a group —$OCF_3$ or a ($C_1$–$C_4$)alkylthio;

$R'_5$ has one of the meanings given for $R_5$ and is in the 5- or 6-position of the indene ring;

$R_6$ is hydrogen or a ($C_1$–$C_4$)alkyl;

$R'_6$ is a ($C_1$–$C_4$)alkyl;

$R_7$ has one of the meanings given for $R_5$, or $R_7$ and $R_9$ together form a group —Y—CH$_2$- bonded to the indole ring in the 7-position by the group Y;

$R_8$ is a phenyl monosubstituted to tetrasubstituted by a substituent selected from a halogen, a (C$_1$–C$_4$)alkyl and a (C$_1$–C$_4$)alkoxy; or a polycyclic radical selected from a naphth-1-yl, a naphth-2-yl, a 1,2,3,4-tetrahydronaphth-1-yl, a 1,2,3,4-tetrahydronaphth-5-yl, an anthryl, a benzofuryl, a benzothien-2-yl, a benzothien-3-yl and a 2-, 3-, 4- or 8-quinolyl, said polycyclic radicals being unsubstituted or monosubstituted or disubstituted by a substituent selected from a (C$_1$–C$_4$)alkyl, a (C$_1$–C$_4$)alkoxy, a (C$_1$–C$_4$)alkylthio, a halogen, a cyano, a hydroxyl, a trifluoromethyl and an imidazol-1-yl;

$R_{10}$ and $R_{11}$ together are a group selected from the groups —CH$_2$—O—CH$_2$—CR$_{12}$R$_{13}$— and —(CH$_2$)$_p$—CR$_{12}$R$_{13}$—, in which the carbon atom substituted by $R_{12}$ and $R_{13}$ is bonded to the nitrogen atom;

$R'_{11}$ is a (C$_1$–C$_4$)alkyl, or $R'_{11}$ and $R'_6$, together with the nitrogen atom to which they are bonded, form a group selected from morpholin-4-yl, thiomorpholin-4-yl, piperidin-1-yl and pyrrolidin-1-yl groups;

$R_{12}$ and $R_{13}$ independently of one another are each hydrogen or a (C$_1$–C$_4$)alkyl;

n is 2, 3, 4 or 5;

p is 2 or 3;

Z is the methyl group or a halogen atom; and

Y is the methylene group or the oxygen atom, with the proviso that, in formula (I), one and only one of the substituents $R_1$, $R_3$ or $R_4$ is the group —COR$_8$, and that:

if $R_1$ is —COR$_8$, $R_3$ is the group —CH$_2$CHR$_{10}$NR$_6$R$_{11}$ or the group —(CH$_2$)$_2$NR'$_6$R'$_{11}$ and $R_4$ has one of the meanings given for $R_5$;

if $R_3$ is —COR$_8$, $R_1$ is a group selected from the groups —CH$_2$CHR$_{10}$NR$_6$R$_{11}$; —CHR$_9$CH$_2$NR'$_6$R'$_{11}$; —(CH$_2$)$_2$NR'$_6$R'$_{11}$ and —(CH$_2$)$_n$Z, $R_4$ has one of the meanings given for $R_5$ and at least one of the groups $R_4$, $R_5$ and $R_7$ is hydrogen; and if $R_4$ is —COR$_8$, $R_1$ is a group selected from the groups —CH$_2$CHR$_{10}$NR$_6$R$_{11}$; —CHR$_9$CH$_2$NR'$_6$R'$_{11}$; —(CH$_2$)$_2$NR'$_6$R'$_{11}$ and —(CH$_2$)$_n$Z and $R_3$ is hydrogen or a (C$_1$–C$_4$)alkyl, and their pharmaceutically acceptable salts.

The preferred compounds of formulae (I) and (I') are those in which $R_2$ or $R'_2$ is hydrogen or the methyl group.

Preferred compounds of formulae (I) and (I') also include those in which $R_8$ is a naphth-1-yl group which is unsubstituted or substituted in the 4-position by a fluorine, a chlorine, a bromine, a methyl, a cyano, a methoxy or an imidazol-1-yl group; a naphth-2-yl group; a benzofur-4-yl group or a benzofur-7-yl group.

The compounds of formulae (I) and (I') in which $R_5$ or $R'_5$ is hydrogen are also preferred compounds according to the invention.

Likewise, the compounds of formulae (I) and (I') in which —NR'$_6$R'$_{11}$ is a morpholin-4-yl group are also preferred compounds.

Particularly preferred compounds of formula (I) are those in which:

$R_2$ is hydrogen or the methyl group;

$R_8$ is a naphth-1-yl group which is unsubstituted or substituted in the 4-position by a fluorine, a chlorine, a bromine, a methyl, a cyano, a methoxy or an imidazol-1-yl group; a naphth-2-yl group; a benzofur-4-yl group or a benzofur-7-yl group;

$R_5$ is hydrogen;

—NR'$_6$R'$_{11}$ is a morpholin-4-yl group; and $R_1$, $R_3$, $R_4$ and $R_7$ are as defined above.

Particularly preferred compounds of formula (I') are those in which:

$R'_2$ is hydrogen or the methyl group;

$R_8$ is a naphth-1-yl group which is unsubstituted or substituted in the 4-position by a fluorine, a chlorine, a bromine, a methyl, a cyano, a methoxy or an imidazol-1-yl group; a naphth-2-yl group; a benzofur-4-yl group or a benzofur-7-yl group;

$R'_5$ is hydrogen;

—NR'$_6$R'$_{11}$ is a morpholin-4-yl group; and $R'_1$, $R'_3$, are as defined above.

Among the compounds of formulae (I) and (I') above, those in which $R_2$ and $R'_2$ are a methyl group are very particularly preferred.

The compounds of formula (I) are indole derivatives substituted in the 1-, 3- or 4-position by an acyl group (—COR$_8$). According to the position of the acyl group, the compounds of formula (I) can be divided into three sub-families of compounds of the following formulae (Ia), (Ib) and (Ic) respectively.

The indoles acylated in the 1-position are the compounds of formula (Ia):

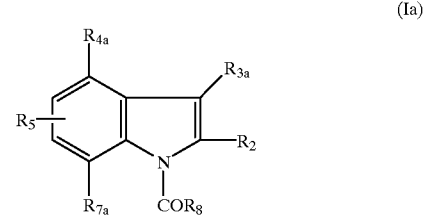

(Ia)

in which:

$R_{3a}$ is the group —CH$_2$CHR$_{10}$NR$_6$R$_{11}$ or the group —(CH$_2$)$_2$NR'$_6$R'$_{11}$;

$R_{4a}$ is hydrogen, a (C$_1$–C$_4$)alkyl, a (C$_1$–C$_4$)alkoxy, a halogen atom, a group —CF$_3$, a group —OCF$_3$ or a (C$_1$–C$_4$)alkylthio;

$R_{7a}$ is hydrogen, a (C$_1$–C$_4$)alkyl, a (C$_1$–C$_4$)alkoxy, a halogen atom, a group —CF$_3$, a group —OCF$_3$ or a (C$_1$–C$_4$)alkylthio; and $R_2$, $R_5$, $R_8$, $R_6$, $R'_6$, $R_{10}$, $R_{11}$ and $R'_{11}$ are as defined above for the compounds of formula (I).

The preferred indole derivatives of formula (Ia) are the compounds in which:

$R_2$ is hydrogen or a methyl group;

$R_{3a}$ is one of the following groups:

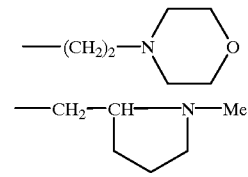

-continued

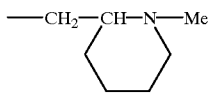

and $R_{4a}$, $R_5$ and $R_{7a}$ are each hydrogen.

The indoles acylated in the 3-position are the compounds of formula (Ib):

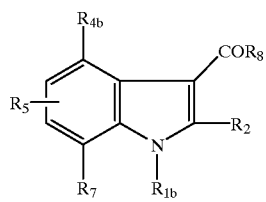
(Ib)

in which $R_{1b}$ is a group of the formula —$CH_2CHR_{10}NR_6R_{11}$; —$(CH_2)_2NR'_6R'_{11}$; —$CHR_9CH_2NR'_6R'_{11}$ or —$(CH_2)_nZ$;

$R_{4b}$ is hydrogen, a ($C_1$–$C_4$)alkyl, a ($C_1$–$C_4$)alkoxy, a halogen atom, a group —$CF_3$, a group —$OCF_3$ or a ($C_1$–$C_4$)alkylthio; and $R_2$, $R_5$, $R_6$, $R_9$, $R_{10}$, $R_{11}$, $R'_6$, $R'_{11}$, n, Z, $R_7$ and $R_8$ are as defined above for the compounds of formula (I).

The preferred indole derivatives of formula (Ib) are the compounds in which:

$R_{1b}$ is a group selected from

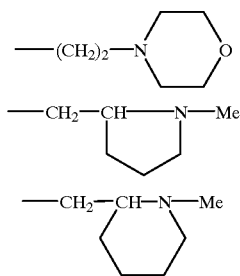

or $R_{1b}$ is a group

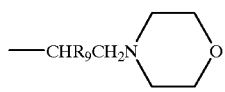

in which $R_9$ together with $R_7$ forms a group —Y—$CH_2$—, in which Y is O or —$CH_2$—, so that $R_{1b}$ is:

a group of the formula:

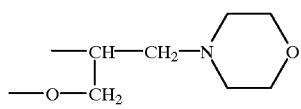

in which the oxygen is bonded to the 7-position of the indole; or a group of the formula:

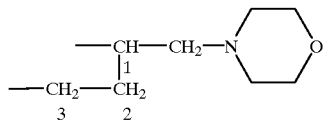

in which the carbon $C_3$ is bonded to the 7-position of the indole;

$R_2$ is hydrogen or the methyl group;

$R_8$ is a naphth-1-yl group which is unsubstituted or substituted in the 4-position by a fluorine, a chlorine, a bromine, a methyl, a cyano, a methoxy or an imidazol-1-yl group; a naphth-2-yl group; a benzofur-4-yl group or a benzofur-7-yl group; and $R_{4b}$, $R_5$ and $R_7$ are as defined above.

The indoles acylated in the 4-position are the compounds of formula (Ic):

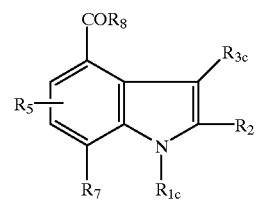
(Ic)

in which:

$R_{1c}$ is a group of the formula —$CH_2CHR_{10}NR_6R_{11}$; —$(CH_2)_2NR'_6R'_{11}$; —$CHR_9CH_2NR'_6R'_{11}$ or —$(CH_2)_nZ$;

$R_{3c}$ is hydrogen or a ($C_1$–$C_4$)alkyl; and $R_2$, $R_5$, $R_6$, $R'_6$, $R_7$, $R_8$, $R_9$, $R_{11}$, $R'_{11}$, n and Z are as defined above for the compounds of formula (I).

The preferred indole derivatives of formula (Ic) are the compounds in which:

$R_{3c}$ and $R_5$ are each hydrogen; and $R_{1c}$, $R_2$, $R_7$ and $R_8$ are as defined above.

Particularly preferred compounds of formula I are:

1-(2-(morpholin-4-yl)ethyl)-2-methyl-3-(naphth-1-ylcarbonyl)-7-methoxyindole;

1-(2-(morpholin-4-yl)ethyl)-2-methyl-3-(4-chloronaphth-1-ylcarbonyl)-7-methoxyindole; and 1-n-pentyl-2-methyl-3-(4-chloronaphth-1-ylcarbonyl)-7-methoxyindole.

The compounds of formulae (I) and (I') according to the invention can be obtained by different methods of synthesis which particularly involve alkylamino group addition, acylation and cyclization steps well known to those skilled in the art. Particularly appropriate methods of obtaining the compounds of the invention are described for example in patents NL 73 09 094, U.S. Pat. No. 5,109,135, U.S. Pat. No. 4,939,138, U.S. Pat. No. 5,081,122, U.S. Pat. No. 4,840,950, EP 0 278 265, U.S. Pat. No. 5,292,736 and U.S. Pat. No. 4,581,354.

These methods are mentioned briefly below.

Thus the compounds of formula (Ia) can be obtained by method A shown in Scheme I below.

This method A, which is described in patent NL 73 09 094, consists in:

1/ reacting a hydrazine of formula (1) with a ketone of the formula $R_2COCH_2R_{3a}$, in which $R_2$ and $R_{3a}$ are as defined above, to form a compound of formula (2);

2/ acylating the resulting compound of formula (2) to form a compound of formula (Ia); and 3/ optionally converting the resulting compound of formula (Ia) to one of its pharmaceutically acceptable salts.

Step 1/ of method A is a Fischer reaction, which is advantageously carried out in an inert solvent such as methanol, ethanol, isopropanol or acetic acid, in the presence of an acid catalyst such as sulfuric acid, hydrochloric acid, glacial acetic acid or zinc chloride, at a temperature between 20° C. and 150° C.

Step 2/ of method A is an acylation reaction, which is advantageously carried out with an acid halide of the formula $R_8COX$, in the presence of a base such as an alkali metal hydroxide, hydride, amide or alcoholate, in an inert organic solvent. Examples of appropriate organic solvents for this type of reaction are toluene, xylene and DMF. The reaction can be carried out at between 0° C. and the boiling point of the solvent used.

The compounds of formula (Ia) can also be obtained by method $A_1$ shown in Scheme II.

This method $A_1$ consists in:

1/ reacting a compound of formula (3) successively with an alkali metal hydride such as sodium hydride, and then with $NH_2Cl$ to form the substituted hydrazine of formula (4);

2/ then reacting the resulting hydrazine with a ketone of the formula $R_2COCH_2R_{3a}$ to form a compound of formula (Ia) by cyclization; and 3/ optionally converting the resulting compound of formula (Ia) to one of its pharmaceutically acceptable salts.

Step 1/ of method $A_1$ is advantageously carried out in an inert solvent such as ethyl ether or THF, at a temperature of 25° C.

Step 2/ of method $A_1$ is a cyclization, which is carried out under the same conditions as those described above for step 1/ of method A.

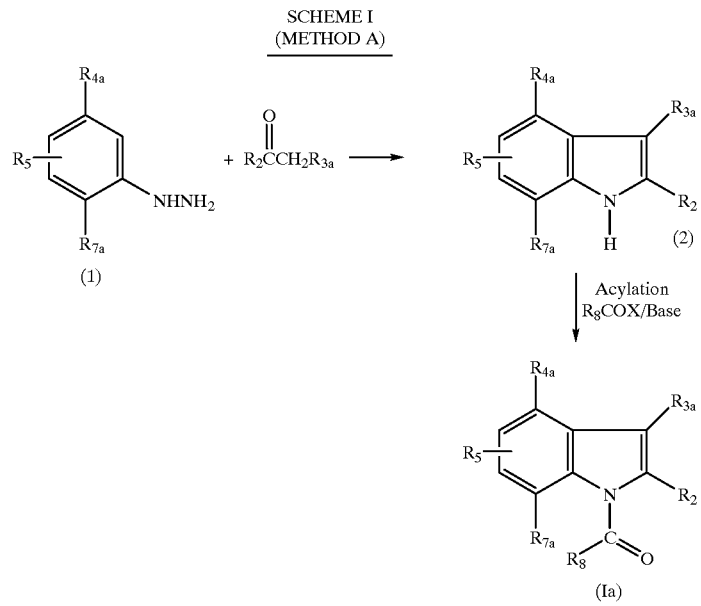

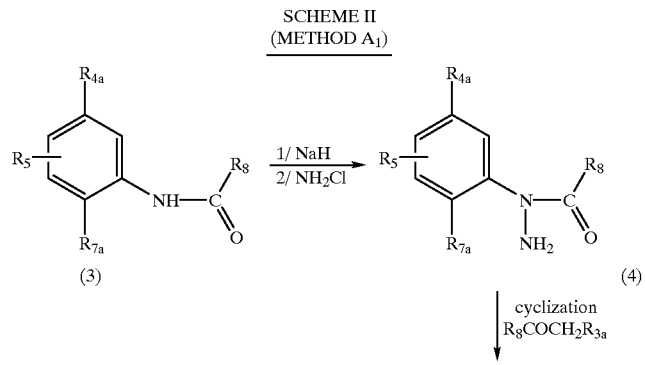

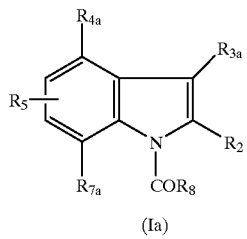

(Ia)

The compounds of formula (Ib) in which $R_{1b}$ is a group selected from —$CH_2CHR_{10}NR_6R_{11}$, —$(CH_2)_2NR'_6R'_{11}$ and —$(CH_2)_nZ$ can be obtained by method B shown in Scheme III below.

This method, which is described especially in patent U.S. Pat. No. 4,581,354, consists in:

1/ reacting an indole derivative of formula (5), appropriately substituted in the 2-position by a group $R_2$ as defined above, with a halide of the formula $XCH_2CHR_{10}NR_6R_{11}$, $X(CH_2)_2NR'_6R'_{11}$ or $X(CH_2)_nZ$, in which $R_6$, $R_{10}$, $R_{11}$, $R'_6$, $R'_{11}$, n and Z are as defined above and X is a halogen atom, for example chlorine, bromine or iodine, to form a compound of formula (6) in which $R_{1b}$ is the group —$CH_2CHR_{10}NR_6R_{11}$, —$(CH_2)_2NR'_6R_{11}$ or $(CH_2)_nZ$;

2/ acylating the resulting compound of formula (6) with an acid halide of the formula $R_8$—CO—X, in which X is a halogen, for example chlorine or bromine, and $R_8$ is as defined above, to form a compound of formula (Ib); and 3/ optionally converting the resulting compound of formula (Ib) to one of its pharmaceutically acceptable salts.

Step 1/ of method B is advantageously carried out in the presence of a base, in an organic solvent which is inert under the reaction conditions. Examples of bases which can be used are an alkali metal carbonate such as sodium carbonate or potassium carbonate, a hydride such as sodium hydride, or an alkali metal hydroxide such as potassium hydroxide, potassium hydroxide being very particularly preferred.

Examples of solvents which can be used are toluene, dimethylformamide (DMF) or dimethyl sulfoxide (DMSO), the latter being preferred. The reaction is carried out at between 0° C. and the boiling point of the solvent.

In particular, if $R_{1b}$ is a group $(CH_2)_nZ$, the reaction can also be carried out in the presence of tris[2-(2-methoxyethoxy)ethyl]amine (TDA-1).

Step 2/ of method B is a Friedel-Crafts acylation reaction carried out in the presence of a Lewis acid such as aluminum chloride, in an inert solvent such as 1,2-dichloroethane or carbon disulfide. The acylation reaction can also be carried out in the presence of a Lewis acid such as ethylmagnesium dichloride, in an inert solvent such as dichloromethane, by the method described in J. Med. Chem. 1995, 38, 3094.

In a variant of step 1/ of method B (method B'), the compound of formula (6) can also be prepared by following the three steps shown in Scheme III' below. This variant consists in reacting an aniline of formula (9) with a ketone of the formula $RSCH_2COR_2$, in which R is a methyl or a phenyl, in the presence of tert-butyl hypochlorite (tBuOCl), by the method described in J. Am. Chem. Soc. 1974, 96, 5495. The resulting compound (10) is then alkylated, under conditions analogous to those described above for step 1/ of method B, to give the compound of formula (11). The sulfur-containing group is then removed by reaction with Raney nickel or by reaction with 2-mercaptobenzoic acid in trifluoroacetic acid, by the method described in Tetrahedron Lett. 1993, 34 (13), 2059–2062, to give the compound of formula (6).

In a variant also described in patent U.S. Pat. No. 4,581,354 (method $B_1$ shown in Scheme IV), the compound (5) is first acylated by reaction with a methylmagnesium halide and an acid halide of the formula $R_8COX$, in ether, to form the compound (7), after which the substituent $R_{1b}$ is added by reacting the compound (7) with a halide $XR_{1b}$ in the presence of a base, under conditions analogous to those described above for step 1/ of method B.

In another variant described in patent EP 0 444 451 (method $B_2$ shown in Scheme V), the compound (5) is treated with a base such as sodium hydride or $K_2CO_3$, and then reacted with mesyl chloride to give the compound (8). The substituent $R_{1b}$ is then added by reacting the compound (8) with a hydroxyalkylamine of the formula $R_{1b}OH$. Finally, the resulting compound (6) is acylated to give the compound Ib.

SCHEME III (METHOD B)
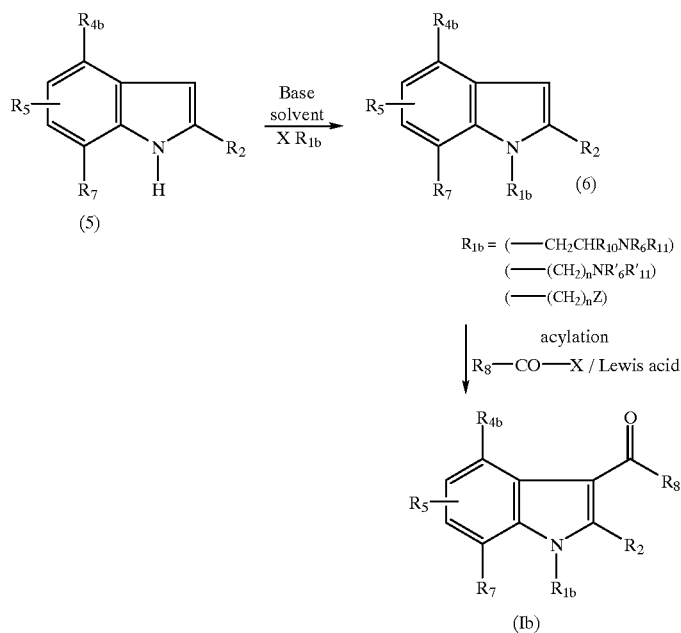
SCHEME III' (METHOD B')
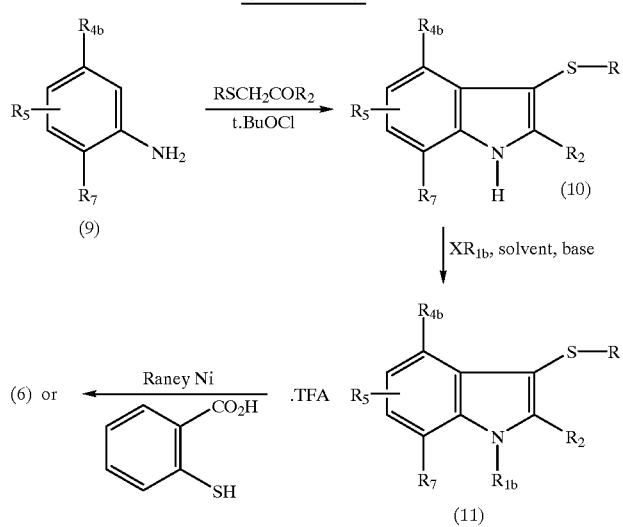

SCHEME IV
(METHOD B₁)

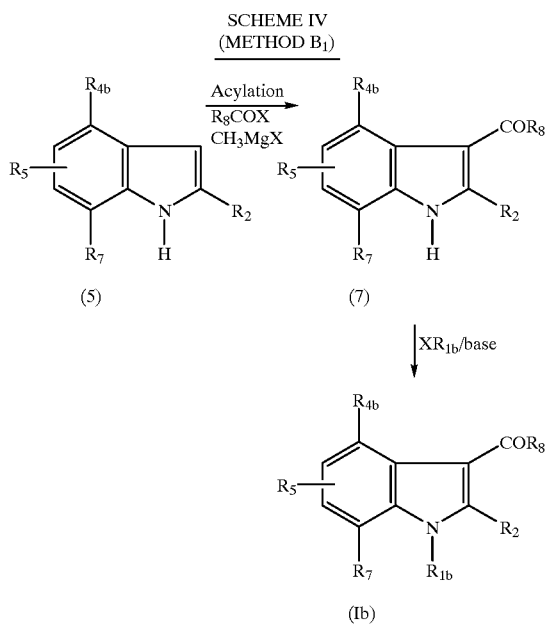

SCHEME V
(METHOD B₂)

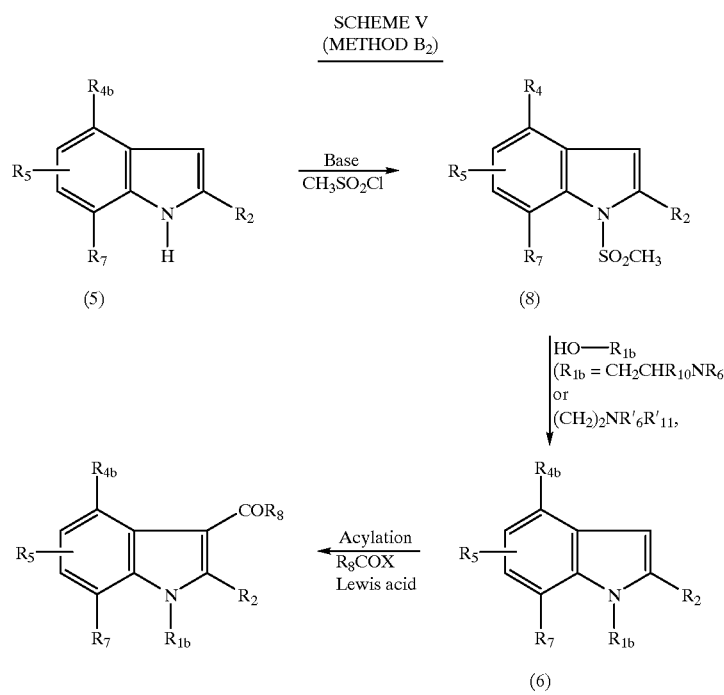

1/ heating a mixture of the compound (1) and potassium carbonate with epichlorohydrin to give the compound (2);

2/ reacting the compound (2) with an appropriate amine of the formula $HNR'_6R'_{11}$ to give the compound (3);

3/ oxidizing the compound (3) to give the compound (4);

4/ reducing and then cyclizing the compound (4), in the presence of a catalyst such as platinum, to give the compound (5);

5/ reacting the compound (5) with an alkali metal nitrite, in an acidic aqueous medium, at a temperature between 0° C. and 10° C., to give the compound (6); and 6/ reducing the resulting compound (6) with hydrogen in the presence of a metal catalyst, or with an alkali metal aluminum hydride such as lithium aluminum hydride, in an inert solvent such as tetrahydrofuran (THF), at a temperature between 0° and the boiling point of the solvent used.

There are two routes, called routes I and II, for preparing the compounds of formula (Ib) from the resulting compound (7).

Route I consists in:

7/ preparing the compound (8) from the compound (7) by means of a Fischer indole synthesis, i.e. by reacting the latter compound with a ketone of the formula $C_6H_5SCH_2COR_2$. This reaction is carried out at a temperature between 20 and 150° C., in an inert organic solvent such as methanol, in the presence of an acid catalyst such as sulfuric acid or glacial acetic acid, the latter generally being preferred;

8/ removing the thiophenyl group from the compound (8) by heating the latter in an organic solvent, in the presence of Raney nickel, at the reflux temperature of the organic solvent, to give the compound (9); and 9/ obtaining the final product (Ib) by reacting the compound (9) with an acid halide of the form $R_8COCl$, in the presence of a Lewis acid such as aluminum chloride, in an inert organic solvent.

The compounds of formula (Ib) in which $R_{1b}$ is a group $-CHR_9CH_2NR'_6R'_{11}$ and $R_9$ together with $R_7$ forms a group $-CH_2-O$, so that $R_{1b}$ is a group

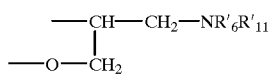

can be obtained by method $B_3$ shown in Scheme VI.

This method, which is described especially in patents U.S. Pat. No. 5,109,135 and U.S. Pat. No. 4,939,138, consists in:

Route II:
This route is a direct way of preparing the compound of formula Ib: It consists in reacting the compound (7) with a diketone of the formula $R_8COCH_2COR_2$ by means of the Fischer reaction described in step 7/ of route I. To obtain the compound (Ib) in optically pure form, the enantiomers of the compound (5) are resolved by the method described in patent U.S. Pat. No. 4,939,138.
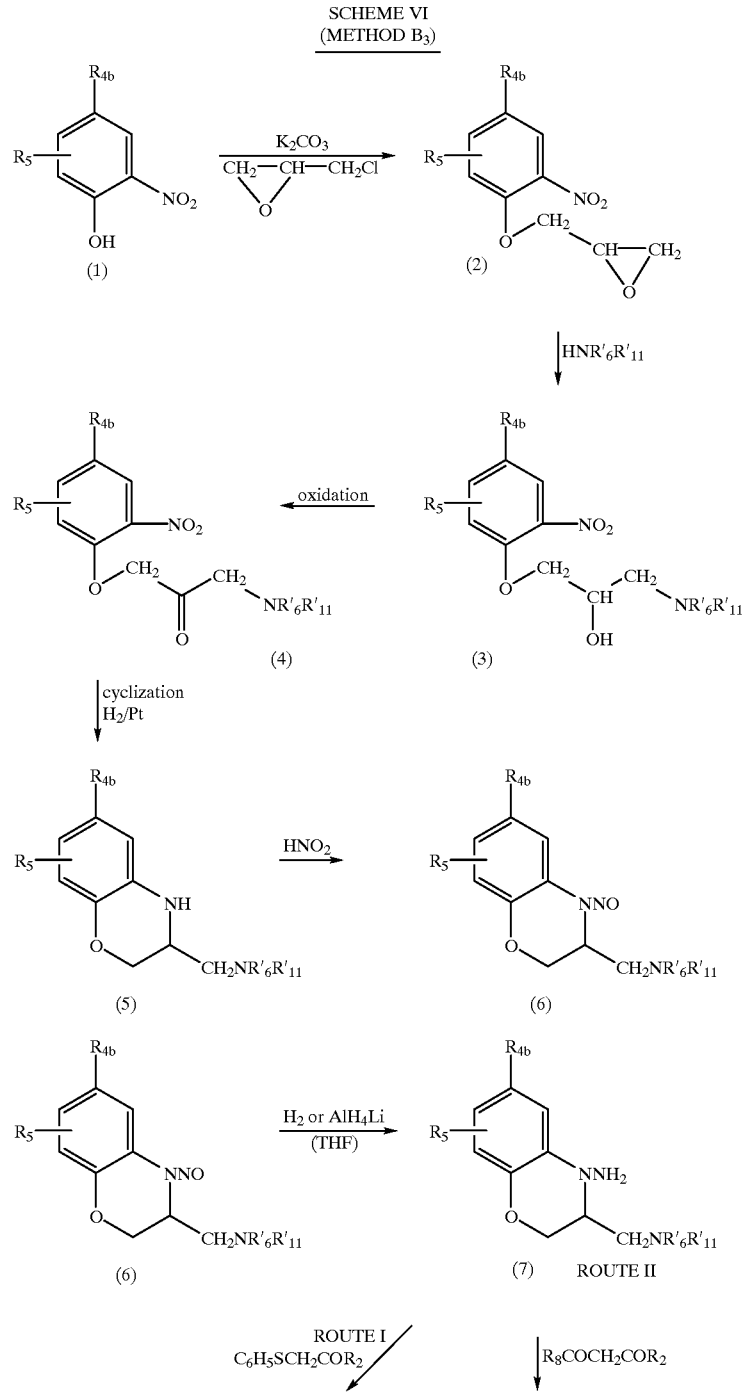

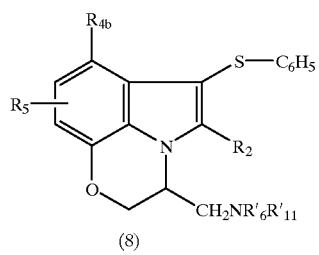

(8)

[H] Raney Nickel ↓

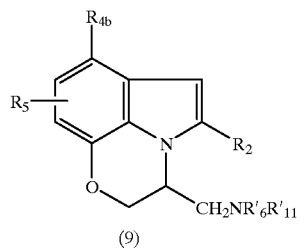 acylation
R₈COCl
AlCl₃
→ 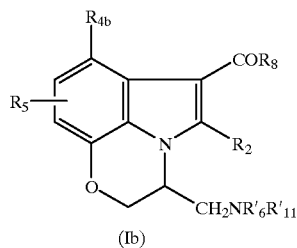

(9)  (Ib)

The compounds of formula Ib in which $R_{1b}$ is a group —$CHR_9CH_2NR'_6R'_{11}$ and $R_9$ together with $R_7$ forms a group —$CH_2$—$CH_2$—, so that $R_{1b}$ is a group

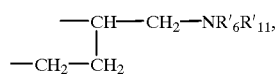

can be obtained by method $B_4$ shown in Scheme VII.

This method consists in:
1/ reacting the quinaldic acid with thionyl chloride in toluene and then adding a compound of the formula $HNR'_6R'_{11}$ to the mixture to give the compound (2);
2/ reducing the compound (2) in toluene, in the presence of the catalyst Red-Al, to give the compound (3); and then
3/ treating the compound (3) as in the previous method $B_3$ (step 5 et seq.) to give the compound of formula Ib.

The first two steps of method $B_4$ are described by Stanton et al. (J. Med. Chem. (1983) 26, 986–989).

SCHEME VII
(METHOD B₄)

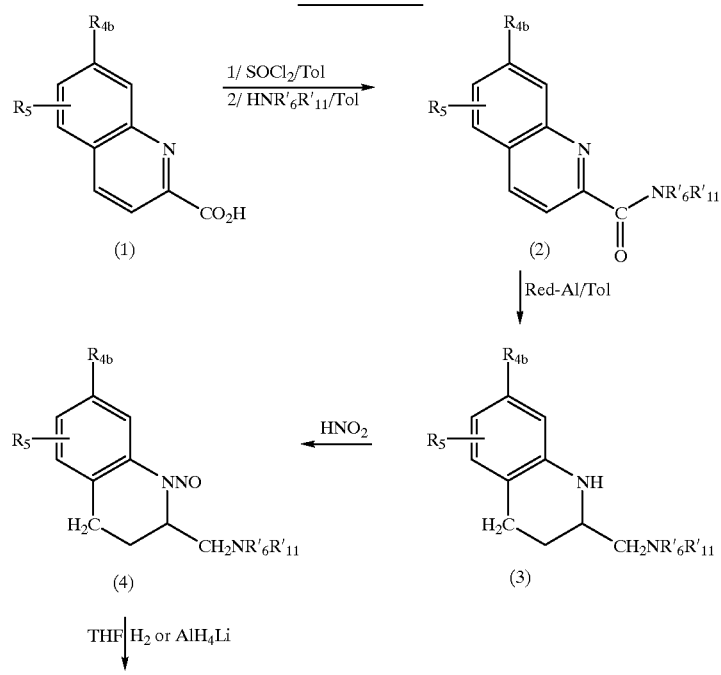

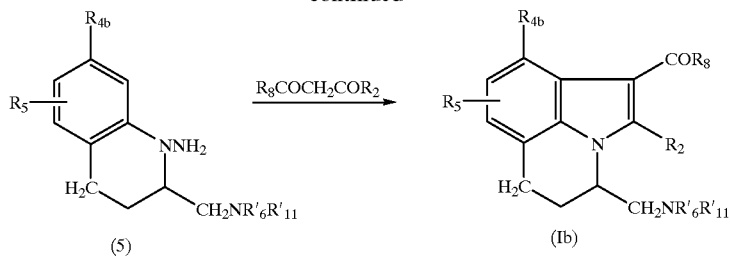

The compounds of formula (Ic) in which $R_{1c}$ is a group $-CH_2CHR_{10}NR_6R_{11}$, $-(CH_2)_2NR'_6R'_{11}$ or $-(CH_2)_nZ$ and $R_{2c}$ and $R_{3c}$ are hydrogen can be obtained by method C (Scheme VIII).

This method, which is described especially in patents U.S. Pat. No. 4,840,950 and EP 0 278 265, consists in:

1/ reacting a 2-methyl-3-nitrobenzoyl halide of formula (1) with a compound of the formula $R_8H$, in which $R_8$ is as defined above, to form a compound of formula (2);

2/ reacting the resulting compound of formula (2) with the dimethylacetal of dimethylformamide to give the compound (3);

3/ cyclizing the resulting compound of formula (3) to form a compound of formula (4); and 4/ reacting the resulting compound (4) with a halogen compound of the formula $XR_{1c}$, in which $R_{1c}$ is as defined above, to form the compound of formula (5).

Step 1 of method C is a Friedel-Crafts reaction, which is carried out in an inert organic solvent such as methylene dichloride, in the presence of aluminum chloride. It is preferable to bring the reactants together at room temperature and then to heat the mixture to the boiling point of the solvent.

Step 2 of method C is preferably carried out by refluxing a solution of the compound of formula (2) with a 2 to 4 mol excess of the dimethylacetal of dimethylformamide in an inert organic solvent such as dimethylformamide or dioxane.

Step 3 of method C is a cyclization reaction of the compound (3), which is advantageously carried out in an inert organic solvent such as ethyl acetate or ethanol, at room temperature. The reaction is carried out under a hydrogen pressure of 50 to 100 psig. The catalysts generally used for this type of reaction are Raney nickel and palladium on charcoal.

Step 4 of method C involves reacting the compound (4) with the appropriate compound $XR_{1c}$ in the presence of a strong base such as sodium hydride. The reaction is advantageously carried out in an inert organic solvent such as DMF, at a temperature between room temperature and the boiling point of the solvent used.

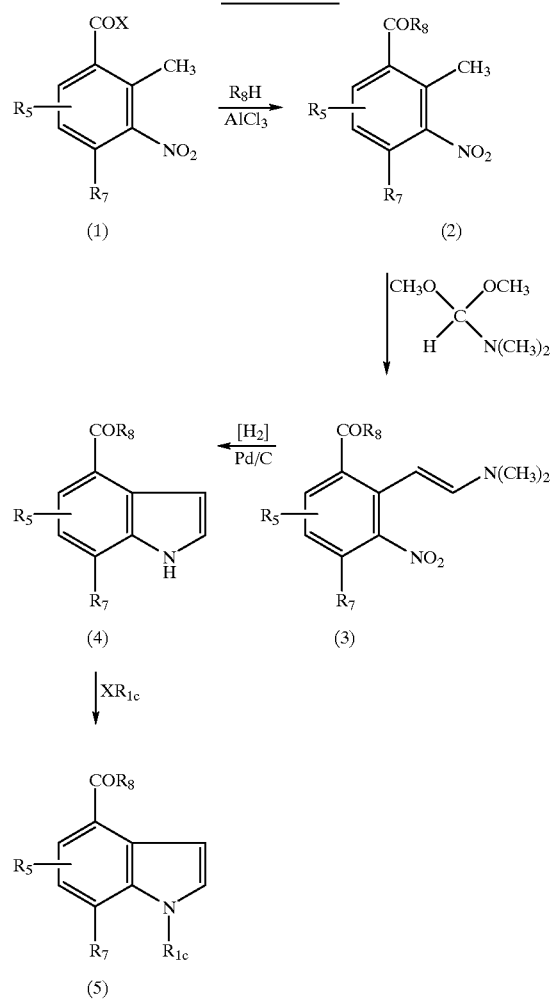

SCHEME VIII
(METHOD C)

The compounds of formulae Ib and Ic (indoles acylated in the 3-position and 4-position respectively) in which $R_{1b}$ and $R_{1c}$ are the group $-CHR_9CH_2NR'_6R'_{11}$ and $R_7$ and $R_9$ form a group $-Y-CH_2-$, in which Y is O or $-CH_2-$, so that $R_{1b}$ and $R_{1c}$ are:

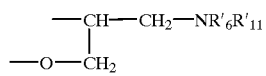

-continued

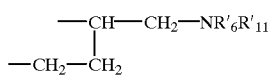

can be obtained by method C, in Scheme IX.

This method consists in acylating the compound (1) with an acid halide $R_8COCl$, in the presence of a Lewis acid such as excess aluminum chloride or ethylaluminum dichloride. This gives the indoles acylated in the 3- and 4-positions, which are then separated.

The compounds of formula (Ic) in which $R_{3c}$ is a $(C_1-C_4)$ alkyl can be obtained by method $C_2$ in Scheme X, which consists in acylating the compounds of formula (1') under the operating conditions of method B in a moderated manner. Method $C_1$ in which Y is O is described in patent U.S. Pat. No. 4,939,138.

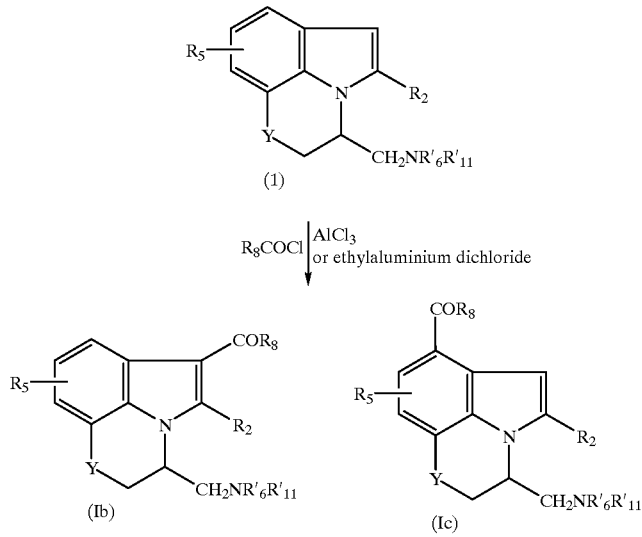

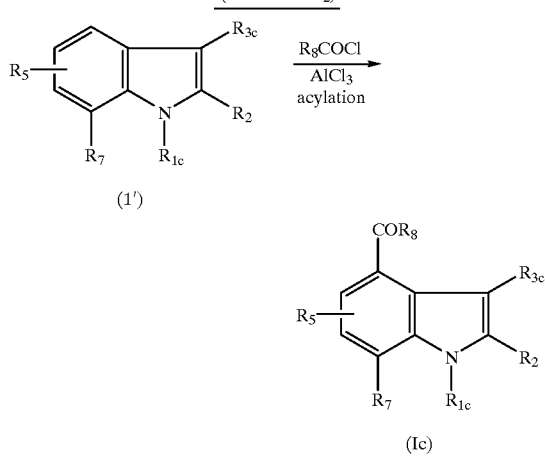

The compounds of formula (I') can be obtained by method D shown in Scheme XI.

This method, which is described especially in patent U.S. Pat. No. 5,292,736, consists in:

1/ treating an indene of formula (1) with a strong base such as n-butyllithium, under an inert atmosphere, in an inert solvent, at a temperature between room temperature and the boiling point of the solvent, and then reacting the resulting compound with an appropriate halide of the formula $XR'_1$, in equimolar proportions, at a temperature between 0° C. and the boiling point of the mixture, under an inert atmosphere, to give the compound (2); and 2/ treating the compound (2) with a strong base such as sodium methylate, and then reacting said compound with an appropriate ketone or aldehyde of the formula

to give the compound (I'). This reaction is advantageously carried out in an inert solvent, at a temperature between room temperature and the boiling point of the solvent used.

SCHEME XI
(METHOD D)

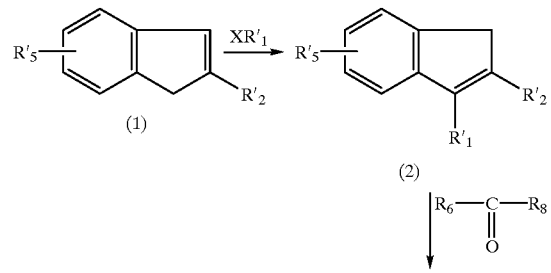

-continued (I')

$R'_3 = CR_6R_8$ $R'_1 = CH_2CHR_{10}NR_6R_{11}$ or $(CH_2)_2NR'_6R'_{11}$

The enantiomers of the compounds of formulae (I) and (I') can be obtained by the conventional methods well known to those skilled in the art. Of the compounds of formulae (I) and (I') described above, the compounds of formulae (Ia) and (Ic) as defined above, and the compounds of formulae $(Ib_1)$, $(Ib_2)$, $(Ib_3)$ and (I'a) below, are novel and constitute a further subject of the invention.

These compounds are:

A/ the compounds of formula $(Ib_1)$:

$(Ib_1)$ in which:

R'$_{1b}$ is a group of the formula —CH$_2$CHR$_{10}$NR$_6$R$_{11}$ or —(CH$_2$)$_2$NR'$_6$R'$_{11}$;

R$_{4b}$ is hydrogen, a (C$_1$–C$_4$)alkyl, a (C$_1$–C$_4$)alkoxy, a halogen atom, a group —CF$_3$, a group —OCF$_3$ or a (C$_1$–C$_4$)alkylthio;

R$_{7b}$ is hydrogen, a (C$_1$–C$_4$)alkyl, a (C$_1$–C$_4$)alkoxy, a halogen atom, a group —CF$_3$, a group —OCF$_3$ or a (C$_1$–C$_4$)alkylthio; and R$_2$, R$_5$, R$_6$, R'$_6$, R$_8$, R$_{10}$, R$_{11}$ and R'$_{11}$ are as defined above for the compounds of formula (I), with the proviso that:

1/ if CH$_2$CHR$_{10}$NR$_6$R$_{11}$ is the group

—CH$_2$—CH—N—CH$_3$;

R$_{4b}$, R$_5$ and R$_{7b}$ are hydrogen and R$_2$ is hydrogen or the methyl group, R$_8$ is other than the naphth-1-yl group;

2/ if CH$_2$CHR$_{10}$NR$_6$R$_{11}$ is the group

—CH$_2$—CH—N—CH$_3$;

R$_{4b}$, R$_5$ and R$_{7b}$ are hydrogen and R$_2$ is methyl, R$_8$ is other than the naphth-1-yl group;

3/ if —(CH$_2$)$_2$NR'$_6$R'$_{11}$ is the group

—(CH$_2$)$_2$—N O,

R$_{7b}$ is the methoxy group, R$_2$ is methyl and R$_{4b}$ and R$_5$ are hydrogen, R$_8$ is other than the naphth-1-yl group; and 4/ if —(CH$_2$)$_2$NR'$_6$R'$_{11}$ is the group

—(CH$_2$)$_2$—N O, and R$_2$, R$_{4b}$, R$_5$ and R$_{7b}$ are hydrogen, R$_8$ is other than the 4-bromonaphth-1-yl group.

B/ the compounds of formula $(Ib_2)$:

$(Ib_2)$ in which:

R"$_{1b}$ is the group —(CH$_2$)$_n$Z;

R$_{4b}$ is hydrogen, a (C$_1$–C$_4$)alkyl, a (C$_1$–C$_4$)alkoxy, a halogen atom, a group —CF$_3$, a group —OCF$_3$ or a (C$_1$–C$_4$)alkylthio;

R$_{7b}$ is hydrogen, a (C$_1$–C$_4$)alkyl, a (C$_1$–C$_4$)alkoxy, a halogen atom, a group —CF$_3$, a group —OCF$_3$ or a (C$_1$–C$_4$)alkylthio; and R$_2$, R$_5$, R$_6$, R'$_6$, R$_8$, R$_{10}$, R$_{11}$ and R'$_{11}$ are as defined above for the compounds of formula (I), with the proviso that if Z is bromine, n is 3 or 4, R$_{4b}$, R$_5$ and R$_{7b}$ are hydrogen and R$_2$ is a methyl group, R$_8$ is other than the naphth-1-yl and 4-methoxyphenyl groups.

C/ the compounds of formula $(Ib_3)$:

$(Ib_3)$ in which:

R'''$_{1b}$ is a group of the formula —CHR$_9$CH$_2$NR'$_6$R'$_{11}$;

R$_{4b}$ is hydrogen, a (C$_1$–C$_4$)alkyl, a (C$_1$–C$_4$)alkoxy, a halogen atom, a group —CF$_3$, a group —OCF$_3$ or a (C$_1$–C$_4$)alkylthio; and R$_2$, R$_5$, R$_6$, R'$_6$, R$_7$, R$_8$, R$_9$, R$_{10}$, and R'$_{11}$ are as defined above for the compounds of formula (I), with the proviso that if $NR'_6R'_{11}$ is the group

Y is oxygen, $R_2$ is the methyl group and $R_{4b}$ and $R_5$ are hydrogen, $R_8$ is other than the naphth-1-yl, 4-bromonaphth-1-yl and 5,7-dibromonaphth-1-yl groups.

D/ the compounds of formula (I'a) are the compounds of formula (I') as defined above, with the proviso that:

1/ if $R'_1$ is the group

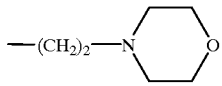

and $R'_2$, $R'_5$ and $R_6$ are hydrogen, $R_8$ is other than the 4-methoxynaphth-1-yl, 4-hydroxynaphth-1-yl and 9-anthryl groups; and 2/ if $R'_1$ is the group

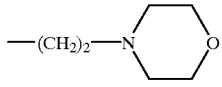

$R'_2$ is methyl and $R'_5$ and $R_6$ are hydrogen, $R_8$ is other than the naphth-1-yl and 4-methoxynaphth-1-yl groups.

Of these compounds, those which are particularly preferred are the compounds below:

1-(2-(morpholin-4-yl)ethyl)-2-methyl-3-(4-fluoronaphth-1-ylcarbonyl)-7-methoxyindole;

1-(2-(morpholin-4-yl)ethyl)-2-methyl-3-(4-chloronaphth-1-ylcarbonyl)-7-methoxyindole;

1-n-pentyl-2-methyl-3-(4-chloronaphth-1-ylcarbonyl)-7-methoxyindole;

(−)-3-(morpholin-4-ylmethyl)-5-methyl-7-(5,7-dibromonaphthylcarbonyl)-2,3-dihydropyrrolo[1,2,3-de]-1,4-benzoxazine methanesulfonate;

(+)-(2-methyl-4-(morpholin-4-ylmethyl)-5,6-dihydro-4H-pyrrolo[3,2,1-ij]-quinolin-1-yl)naphthalen-1-ylmethanone methanesulfonate;

1-(naphth-1-ylcarbonyl)-3-(2-(morpholin-4-yl)ethyl)indole methanesulfonate;

1-(2-(morpholin-4-yl)ethyl)-2-methyl-3-(4-bromonaphth-1-ylcarbonyl)-7-methoxyindole;

1-n-pentyl-2-methyl-3-(4-bromonaphth-1-ylcarbonyl)-7-methoxyindole;

1-(2-(morpholin-4-yl)ethyl)-2-methyl-3-(naphth-1-ylcarbonyl)-7-(trifluoromethyl)indole;

1-(2-(morpholin-4-yl)ethyl)-2-methyl-3-(4-bromonaphth-1-ylcarbonyl)-7-(trifluoromethyl)indole;

1-(2-(morpholin-4-yl)ethyl)-2-methyl-3-(4-bromonaphth-1-ylcarbonyl)-7-fluoroindole;

1-n-pentyl-2-methyl-3-(4-bromonaphth-1-ylcarbonyl)-7-fluoroindole; and 1-(2-(morpholin-4-yl)ethyl)-2,7-dimethyl-3-(4-bromonaphth-1-ylcarbonyl)-indole.

The compounds useful for the preparation of drugs according to the invention are generally administered in dosage units. Said dosage units are preferably formulated in pharmaceutical compositions in which the active principle is mixed with a pharmaceutical excipient.

According to another feature, the present invention relates to pharmaceutical compositions which contain, as the active principle, a compound of formula (I) or (I') having a high affinity for the human $CB_2$ receptor, said affinity being characterized by an inhibition constant Ki which is less than or equal to 10 nM in ligand binding studies; the present invention relates very particularly to pharmaceutical compositions in which a compound of formula (Ia), ($Ib_1$), ($Ib_2$), ($Ib_3$), (Ic) or (I'a) is present as the active principle.

The compounds of formula (I) or (I') and their pharmaceutically acceptable salts can be used in daily doses of 0.1 to 100 mg per kilogram of body weight of the mammal to be treated, preferably in daily doses of 0.2 to 50 mg/kg. In humans the dose can preferably vary from 0.5 to 1000 mg per day, more particularly from 1 to 500 mg, depending on the age of the subject to be treated or the type of treatment: prophylactic or curative.

The diseases which can be treated by the compounds and their pharmaceutically acceptable salts are, for example, autoimmune diseases, infectious diseases and allergic diseases. The following autoimmune diseases may be mentioned more particularly: systemic lupus erythematosus, connective tissue diseases, Sjögren's syndrome, ankylosing spondylarthritis, reactive arthritis, undifferentiated spondylarthritis, Behcet's disease and hemolytic autoimmune anemia. The allergic diseases to be treated can be of the immediate hypersensitivity or asthma type, for example. Likewise, the compounds and their pharmaceutically acceptable salts can be used to treat vascularitis, parasitic infections, amyloidosis and diseases affecting the plasmacyte line.

In the pharmaceutical compositions of the present invention for oral, sublingual, subcutaneous, intramuscular, intravenous, transdermal, local or rectal administration or administration by inhalation, the active principles can be administered to animals and humans in unit forms of administration, mixed with conventional pharmaceutical carriers. The appropriate unit forms of administration can be chosen according to the diseases to be treated; they include oral forms such as tablets, gelatin capsules, powders, granules and solutions or suspensions to be taken orally, forms of administration by inhalation, sublingual and buccal forms of administration, subcutaneous, intramuscular, intravenous, intranasal or intraocular forms of administration and rectal forms of administration. The oral or intravenous forms of administration or the forms of administration by inhalation are preferred.

When a solid composition is prepared in the form of tablets, the main active principle is mixed with a pharmaceutical vehicle such as gelatin, starch, lactose, magnesium stearate, talcum, gum arabic or the like. The tablets can be coated with sucrose or other appropriate substances, or else they can be treated so as to have a prolonged or delayed activity and so as to release a predetermined amount of active principle continuously.

A preparation in the form of gelatin capsules is obtained by mixing the active principle with a diluent and pouring the resulting mixture into soft or hard gelatin capsules.

A preparation in the form of a syrup or elixir can contain the active principle together with a sweetener, which is preferably calorie-free, methylparaben and propylparaben as antiseptics, a flavoring and an appropriate color.

The water-dispersible powders or granules can contain the active principle mixed with dispersants, wetting agents or suspending agents, such as polyvinylpyrrolidone, as well as with sweeteners or taste correctors. Rectal administration is effected using suppositories, which are prepared with binders melting at the rectal temperature, for example cocoa butter or polyethylene glycols.

Parenteral, intranasal or intraocular administration is effected using aqueous suspensions, isotonic saline solutions or injectable solutions containing pharmacologically compatible dispersants and/or wetting agents, for example propylene glycol or butylene glycol.

Administration by inhalation is effected using an aerosol containing sorbitan trioleate or oleic acid, for example, together with trichlorofluoromethane, dichlorofluoromethane, dichlorotetrafluoroethane or any other biologically compatible propellant gas.

The active principle can also be formulated as microcapsules, optionally with one or more carriers or additives.

In each dosage unit, the active principle of formula (I) or (I') is present in the amounts appropriate to the daily doses envisaged. In general, each dosage unit is suitably adjusted according to the dosage and the intended type of administration, for example tablets, gelatin capsules and the like, sachets, ampoules, syrups and the like, and drops, so that such a dosage unit contains from 0.5 to 1000 mg of active principle, advantageously from 1 to 500 mg and preferably from 1 to 200 mg, to be administered one to four times a day.

The above-mentioned compositions can also contain other active products useful for the desired therapeutics, for example corticosteroids and $\beta_2$-agonists.

By virtue of their very strong affinity for the human $CB_2$ receptor and their high selectivity, the compounds according to the invention may be used in radiolabeled form as laboratory reagents.

For example, they make it possible to characterize, identify and locate the human $CB_2$ receptor in tissue sections or the $CB_2$ receptor in the whole animal by autoradiography.

The compounds according to the invention also make it possible to sort or screen molecules according to their affinity for the human $CB_2$ receptor. This is done by means of a reaction to displace the radiolabeled ligand, forming the subject of the present invention, from its human $CB_2$ receptor.

Examples of appropriate compounds for the purposes of the invention are the compounds described in Examples 1 to 13 below and the compounds shown in Tables 1 to 6, the compounds of Examples 1 to 13 also being listed in these Tables.

The following abbreviations are used in the Examples below:
RT: room temperature
M.p.: melting point
Pd/C: palladium on charcoal
Pt: platinum
DCM: dichloromethane
THF: tetrahydrofuran
DMF: dimethylformamide
DMSO: dimethyl sulfoxide
AcOEt: ethyl acetate
MeOH: methanol
Me: methyl
iPr: isopropyl
Bu: n-butyl
HCl: hydrochloric acid
TFA: trifluoroacetic acid
NaCl: sodium chloride
NaH: sodium hydride
SOCl$_2$: thionyl chloride
AlCl$_3$: aluminum chloride
KOH: potassium hydroxide
TDA-1: tris[2-(2-methoxyethoxy)ethyl]amine
Red-Al: sodium bis(2-methoxyethoxy)aluminum hydride
MgSO$_4$: magnesium sulfate
LiAlH$_4$: lithium aluminum hydride
NaOH: sodium hydroxide
NH$_4$Cl: ammonium chloride
iso ether: diisopropyl ether
ether: diethyl ether
Na$_2$CO$_3$: sodium carbonate
K$_2$CO$_3$: potassium carbonate

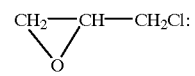

epichlorhydrin
s: singlet
t: triplet
m: multiplet

EXAMPLE 1

1-(2-(Morpholin-4-yl)ethyl)-2-methyl-3-(4-fluoronaphth-1-ylcarbonyl)-7-methoxyindole A/ 2-Methyl-3-(4-fluoronaphth-1-ylcarbonyl)-7-methoxyindole A solution of 1.02 g of 2-methyl-7-methoxyindole in 5 ml of ether is added dropwise to 2.60 ml of a 3.0 M solution of methylmagnesium bromide in ether.

The mixture is diluted in 6 ml of ether and cooled to 0° C. It is stirred for 1 hour at room temperature and then cooled to 0° C. A suspension of 4-fluoro-1-naphthoyl chloride in a solution composed of 6 ml of ether and 4 ml of THF is added dropwise to the mixture obtained above.

The mixture is subsequently stirred for 16 hours at room temperature and then for 2 hours under reflux.

It is then hydrolyzed with 50 ml of iced water to which 50 ml of saturated NH$_4$Cl solution have been added.

The solvents are evaporated off under vacuum and the aqueous phase is extracted with DCM and then washed with water. It is dried over MgSO$_4$.

The solvents are evaporated off and the product obtained is then purified by chromatography on silica gel using CH$_2$Cl$_2$ as the eluent.

This gives 0.48 g of the title product (m.p.=170° C.).

B/ 1-(2-(Morpholin-4-yl)ethyl)-2-methyl-3-(4-fluoronaphth-1-ylcarbonyl)-7-methoxyindole 0.28 g of sodium hydride (60% dispersion in oil) is added to a solution of 0.67 g of the product obtained in A/ in 7 ml of DMF. The mixture is then stirred for 10 min at room temperature.

A suspension of 4-(2-chloroethyl)morpholine hydrochloride in 3 ml of DMF is added to this mixture.

The mixture is heated for 16 hours at 100° C. and then poured into 100 ml of saturated NH$_4$Cl solution at 0° C. It is extracted with DCM, washed with water and dried over MgSO$_4$.

The solvents are evaporated off and the residue is then purified by chromatography on silica gel using an AcOEt/toluene mixture (gradient: 1:1 to 6:4) as the eluent to give 0.43 g of the title compound (m.p.=175° C.).

EXAMPLE 2

1-(2-(Morpholin-4-yl)ethyl)-2-methyl-3-(4-chloronaphth-1-ylcarbonyl)-7-methoxyindole A/ 2-Methyl-3-(4-chloronaphth-1-ylcarbonyl)-7-methoxyindole The procedure is the same as above (Example 1, step A/) except that a suspension of 4-chloro-1-naphthoyl chloride is used as the acid chloride to form the above indole (m.p.=184° C.).

B/ 1-(2-(Morpholin-4-yl)ethyl)-2-methyl-3-(4-chloronaphth-1-ylcarbonyl)-7-methoxyindole The procedure is the same as above (EXAMPLE 1, step B/) except that the product obtained in step A/ above is used as the starting material to form the title compound (m.p.= 149° C.).

EXAMPLE 3

1-n-Pentyl-2-methyl-3-(4-chloronaphth-1-ylcarbonyl)-7-methoxyindole 0.13 g of NaH (60% dispersion in oil) is added to a solution of 0.77 g of the indole prepared in step A/ of Example 2 in 10 ml of DMF.

The mixture is stirred for 10 min, 0.43 ml of 1-iodopentane is then added and the mixture is heated at 100° C. for 16 hours. It is then poured into 100 ml of saturated $NH_4Cl$ solution at 0° C. and extracted with ethyl acetate.

The organic phase is washed with water, dried over $MgSO_4$ and then purified by chromatography on silica gel (eluent=toluene). The product crystallizes from a DCM/$iPr_2O$ mixture, m.p.=112° C.

This gives 0.34 g of the title product (m.p.=112° C.).

EXAMPLE 4

(−)-3-(Morpholin-4-ylmethyl)-5-methyl-7-(5,7-dibromonaphthylcarbonyl)-2,3-dihydropyrrolo[1,2,3-de]-1,4-benzoxazine methanesulfonate 20 ml of ethylaluminum chloride are added dropwise to a solution of 4.09 g of (+)-3-(morpholin-4-ylmethyl)-5-methyl-2,3-dihydropyrrolo[1,2,3-de]-1,4-benzoxazine (obtained as in Preparation 5B of patent U.S. Pat. No. 4,939,138) and 5.19 g of 5,7-dibromo-1-naphthoyl chloride in 100 ml of DCM, cooled to 10° C. The mixture is subsequently stirred for 30 min at 10° C. and then poured into 100 ml of iced water rendered basic with 35% sodium hydroxide solution. The mixture is extracted with DCM, washed with water and dried over $MgSO_4$ and the solvents are evaporated off to give, after purification by chromatography on silica gel (eluent=ether/hexane 70:30), 1.00 g of a less polar product, which is dissolved in the minimum volume of acetonitrile. 2 g of methanesulfonic acid, dissolved in 1 ml of ether beforehand, are added. The crystals obtained are filtered off and then recrystallized from a $CHCl_3$/MeOH mixture to finally give 0.37 g of the title product ($[\alpha]_D$=82.6° (1%, DMF); m.p.=258° C.).

EXAMPLE 5

(+)-(2-Methyl-4-(morpholin-4-ylmethyl)-5,6-dihydro-4H-pyrrolo[3,2,1-ij]-quinolin-1-yl)naphthalen-1-ylmethanone methanesulfonate A/ 2-(Morpholin-4-ylcarbonyl)quinoline This compound is obtained by the procedure described in J. Med. Chem. 26, 986 (1983) using quinaldic acid as the starting material.

(M.p.=105° C.).

B/ (+)-2-(Morpholin-4-ylmethyl)-1,2,3,4-tetrahydroquinoline 101 ml of a 3.4 M solution of Red-Al in toluene are added dropwise to a solution of 16.56 g of the amide obtained above in 350 ml of toluene.

The mixture is then refluxed for 16 hours. After cooling in an ice bath, 250 ml of a semisaturated solution of Rochelle salt (sodium potassium tartrate) are added to the mixture, which is then stirred for a further 30 min.

It is extracted with ether, washed with water and dried over $MgSO_4$ and the solvents are evaporated off.

After crystallization from ethanol, 11.76 g of a yellow solid are obtained; this is resolved with dibenzoyltartaric acid as described in patent U.S. Pat. No. 5,109,135.

(M.p.=88° C.; $[\alpha]_D$=+99° (1%, DMF)).

C/ 1-Amino-2-(morpholin-4-ylmethyl)-1,2,3,4-tetrahydroquinoline

This compound is obtained by the procedure described in patent U.S. Pat. No. 5,109,135 (Preparations 2 and 3) from the amine obtained in the previous step. This product is used without purification in the next step.

D/ (+)-(2-Methyl-4-(morpholin-4-ylmethyl)-5,6-dihydro-4H-pyrrolo[3,2,1-ij]-quinolin-1-yl)naphthalen-1-ylmethanone methanesulfonate This compound is prepared by reaction of the above hydrazine with 4-(naphth-1-yl)butane-2,4-dione by the procedure described in patent U.S. Pat. No. 5,109,135 (Example 2), followed by salification with methanesulfonic acid in ether and crystallization from ethanol ($[\alpha]_D$=+11.7° (1%, DMF); m.p.=250° C.).

EXAMPLE 6

1-(Naphth-1-ylcarbonyl)-3-(2-(morpholin-4-yl)ethyl) indole methanesulfonate

This compound is prepared by reacting 3-[2-(morpholin-4-yl)ethyl]indole (D. L. Nelson et al., Adv. Biochem. Psychopharmacol. (1993) 37, 337) with naphth-1-ylcarboxylic acid chloride, in the presence of NaH in DMF, by the procedure described in patent NL 73 08094 (Example 1) (m.p.=187° C.).

EXAMPLE 7

1-(2-(Morpholin-4-yl)ethyl)-2-methyl-3-(4-bromonaphth-1-ylcarbonyl)-7-methoxyindole A/ 2-Methyl-3-(4-bromonaphth-1-ylcarbonyl)-7-methoxyindole 14.7 ml of a 3 M solution of methylmagnesium bromide in ether, diluted in 30 ml of ether, are cooled to 0° C., a solution of 5.6 g of 2-methyl-7-methoxyindole in 25 ml of ether is added dropwise and the mixture is then stirred for 1 hour at RT. A solution of 12.3 g of 4-bromo-1-naphthoyl chloride in 28 ml of ether and 19 ml of THF is then added and the reaction mixture is refluxed for 1 hour and stirred for 16 hours at RT. It is poured into 350 ml of iced water, 40 g of $NH_4Cl$ are added and the solvents are concentrated under vacuum. The aqueous phase is extracted with ether, the organic phase is washed with 50 ml of saturated $NH_4Cl$ solution and with 100 ml of saturated NaCl solution and dried over $MgSO_4$ and the solvent is evaporated off under vacuum. The residue is chromatographed on silica gel using DCM as the eluent to give 2 g of the expected product after recrystallization from toluene.

B/ 1-(2-(Morpholin-4-yl)ethyl)-2-methyl-3-(4-bromonaphth-1-ylcarbonyl)-7-methoxyindole This compound is prepared by the procedure described in step B of EXAMPLE 1 from 0.8 g of the compound obtained in the previous step, 0.28 g of NaH as a 60% dispersion in oil, 7 ml of DMF and a suspension of 0.64 g of 4-(2-chloroethyl)-morpholine hydrochloride in 5 ml of DMF. 0.86 g of the expected product is obtained after crystallization from iso ether (m.p.=123–125° C.).

EXAMPLE 8

1-n-Pentyl-2-methyl-3-(4-bromonaphth-1-ylcarbonyl)-7-methoxyindole

A mixture of 0.46 g of the compound obtained in step A of EXAMPLE 7, 0.49 g of 1-iodopentane, 0.16 g of TDA-1 and 0.16 g of ground KOH in 7 ml of toluene is heated at 90° C. for 2 hours. The reaction mixture is poured into 20 ml of water; after decantation, the organic phase is washed with 10% HCl solution, with water and with saturated NaCl solution and dried over $MgSO_4$ and the solvent is evaporated off under vacuum. The residue is chromatographed on silica gel using an AcOEt/toluene mixture (50/50; v/v) as the eluent to give 0.5 g of the expected product (m.p.=114.5° C.).

EXAMPLE 9

1-(2-(Morpholin-4-yl)ethyl)-2-methyl-3-(naphth-1-ylcarbonyl)-7-(trifluoromethyl)indole A/ 2-Methyl-3-(methylthio)-7-(trifluoromethyl)indole A solution of 15 g of 2-(trifluoromethyl)aniline in 300 ml of DCM is cooled to –65° C. under a nitrogen atmosphere, a solution of 11.5 ml of tert-butyl hypochlorite in 30 ml of DCM is added dropwise and the mixture is stirred for 10 minutes. A solution of 9.66 g of (methylthio)acetone in 30 ml of DCM is then added at –65° C. and the mixture is stirred for 2 hours at –65° C. The temperature is allowed to rise to –40° C., a solution of 12.9 ml of triethylamine in 30 ml of DCM is added and the mixture is stirred, the temperature being allowed to rise to RT. The mixture is hydrolyzed by the addition of 200 ml of water; after decantation, the organic phase is washed with water and with saturated NaCl solution and dried over $MgSO_4$ and the solvent is evaporated off under vacuum. The residue is chromatographed on silica gel using toluene as the eluent to give 9.9 g of the expected product.

B/ 2-Methyl-7-(trifluoromethyl)indole 12.4 g of 2-mercaptobenzoic acid are added at RT to a solution of 9.9 g of the compound obtained in the previous step in 100 ml of TFA and the reaction mixture is stirred for 1 hour at RT. It is concentrated under vacuum, the residue is extracted with AcOEt, the organic phase is washed with 1 N NaOH solution, with water and with saturated NaCl solution and dried over $MgSO_4$ and the solvent is evaporated off under vacuum to give 7.36 g of the expected product.

C/ 1-(2-(Morpholin-4-yl)ethyl)-2-methyl-7-(trifluoromethyl)indole 2.25 g of finely ground KOH are added at RT to a solution of 2.8 g of 4-(2-chloroethyl)morpholine hydrochloride in 15 ml of DMSO and the mixture is stirred for 5 minutes at RT. A solution of 2 g of the compound obtained in the previous step in 15 ml of DMSO is then added dropwise and the reaction mixture is stirred for 2 hours at RT and then heated at 100° C. for 18 hours. It is poured into 300 ml of iced water and extracted with DCM, the organic phase is washed with water and with saturated NaCl solution and dried over $MgSO_4$ and the solvent is evaporated off under vacuum. The residue is chromatographed on silica gel using an AcOEt/hexane mixture (from 30/70; v/v to 40/60; v/v) as the eluent to give 2.42 g of the expected product (m.p.=72° C.).

D/ 1-(2-(Morpholin-4-yl)ethyl)-2-methyl-3-(naphth-1-ylcarbonyl)-7-(trifluoromethyl)indole A solution of 0.4 g of the compound obtained in the previous step and 0.2 ml of 1-naphthoyl chloride in 10 ml of DCM is cooled to 0° C. under a nitrogen atmosphere, 1.54 ml of a 1.8 M solution of ethylaluminum dichloride in toluene are added dropwise and the reaction mixture is stirred for 24 hours at RT. It is poured into 100 ml of iced water and extracted with DCM, the organic phase is washed with 5% $Na_2CO_3$ solution, with water and with saturated NaCl solution and dried over $MgSO_4$ and the solvent is evaporated off under vacuum. The residue is chromatographed on silica gel using an AcOEt/hexane mixture (30/70; v/v) as the eluent to give 0.3 g of the expected product after crystallization from iso ether (m.p.=104° C.).

EXAMPLE 10

1-(2-(Morpholin-4-yl)ethyl)-2-methyl-3-(4-bromonaphth-1-ylcarbonyl)-7-(trifluoromethyl) indole This compound is prepared by the procedure described in step D of EXAMPLE 9 from 0.8 g of the compound obtained in step C of EXAMPLE 9, 0.92 g of 4-bromo- 1-naphthoyl chloride in 20 ml of DCM and 3.1 ml of a 1.8 M solution of ethylaluminum dichloride in toluene. 0.9 g of the expected product is obtained (m.p.=160° C.).

EXAMPLE 11

1-(2-(Morpholin-4-yl)ethyl)-2-methyl-3-(4-bromonaphth-1-ylcarbonyl)-7-fluoroindole A/ 2-Methyl-3-(methylthio)-7-fluoroindole This compound is prepared by the procedure described in step A of EXAMPLE 9 from 20 g of 2-fluoroaniline in 600 ml of DCM, 23.4 g of tert-butyl hypochlorite, 22.5 g of (methylthio)acetone and 30 ml of triethylamine. 20.5 g of the expected product are obtained.

B/ 2-Methyl-7-fluoroindole 16 g of 2-mercaptobenzoic acid are added at RT to a solution of 10 g of the compound obtained in the previous step in 100 ml of TFA and the mixture is stirred for 2 hours at RT. The insoluble material is filtered off and the filtrate is concentrated under vacuum. The residue is taken up with 100 ml of an AcOEt/water mixture (50/50; v/v), the organic phase is washed three times with 10% NaOH solution, with water, with 10% HCl solution and with saturated NaCl solution and dried over $MgSO_4$ and the solvent is evaporated off under vacuum. The residue is chromatographed on silica gel using toluene as the eluent to give 3.8 g of the expected product.

C/ 1-(2-(Morpholin-4-yl)ethyl)-2-methyl-7-fluoroindole

A mixture of 1.3 g of the compound obtained in the previous step, 2.76 g of 4-(2-chloroethyl)morpholine hydrochloride, 2.05 g of finely ground KOH and 0.13 g of potassium iodide in 13 ml of DMSO is heated at 100° C. for 16 hours. After cooling to RT, the reaction mixture is poured into 100 ml of water and extracted with toluene, the organic phase is washed with water and with saturated NaCl solution and dried over $MgSO_4$ and the solvent is evaporated off under vacuum. The residue is chromatographed on silica gel using an AcOEt/toluene mixture (50/50; v/v) as the eluent to give 1.3 g of the expected product.

D/ 1-(2-(Morpholin-4-yl)ethyl)-2-methyl-3-(4-bromonaphth-1-ylcarbonyl)-7-fluoroindole This compound is prepared by the procedure described in step D of EXAMPLE 9 from 1.3 g of the compound obtained in the previous step, 1.8 g of 4-bromo-1-naphthoyl chloride in 50 ml of DCM and 6 ml of a 1.8 M solution of ethylaluminum dichloride in toluene. The evaporation residue is chromatographed on silica gel using an AcOEt/toluene mixture (75/25; v/v) as the eluent to give 1 g of the expected product (m.p.=66–67° C).

EXAMPLE 12

1-n-Pentyl-2-methyl-3-(4-bromonaphth-1-ylcarbonyl)-7-fluoroindole

A/ 1-n-Pentyl-2-methyl-7-fluoroindole

A mixture of 1 g of the compound obtained in step B of EXAMPLE 11, 1.6 g of 1-iodopentane, 0.21 g of TDA-1 and 0.75 g of finely ground KOH in 15 ml of toluene is heated at 95° C. for 5 hours. After cooling to RT, 30 ml of water are added, the mixture is decanted, the organic phase is washed with 10% HCl solution, with water and with saturated NaCl solution and dried over $MgSO_4$ and the solvent is evaporated off under vacuum. The residue is chromatographed on silica gel using a cyclohexane/toluene mixture (60/40; v/v) as the eluent to give 0.58 g of the expected product.

B/ 1-n-Pentyl-2-methyl-3-(4-bromonaphth-1-ylcarbonyl)-7-fluoroindole

This compound is prepared by the procedure described in step D of EXAMPLE 9 from 0.58 g of the compound obtained in the previous step, 0.95 g of 4-bromo-1-naphthoyl chloride in 25 ml of DCM and 3.17 ml of a 1.8 M solution of ethylaluminum dichloride in toluene. The evaporation residue is chromatographed on silica gel using an AcOEt/toluene mixture (50/50; v/v) as the eluent to give 0.27 g of the expected product.

NMR (200 MHz); DMSO (2.5 ppm); DOH (3.3 ppm); 0.85 ppm: t: 3H; 1.3 ppm: m: 4H; 1.75 ppm: m: 2H; 2.35 ppm: s: 3H; 4.3 ppm: t: 2H; 6.8–8.4: m: 9H.

EXAMPLE 13

1-(2-(Morpholin-4-yl)ethyl)-2,7-dimethyl-3-(4-bromonaphth-1-ylcarbonyl)indole A/ 2,7-Dimethyl-3-(phenylthio)indole A solution of 21.4 g of 2-methylaniline in 600 ml of DCM is cooled to –70° C. under a nitrogen atmosphere, 21.7 g of tert-butyl hypochlorite are added dropwise and the mixture is stirred for 5 minutes. A solution of 24.9 g of (phenylthio)acetone in 50 ml of DCM is then added at –70° C. and the mixture is stirred for 2 hours at –65° C. 25.3 g of triethylamine are then added at –65° C. and the mixture is stirred, the temperature being allowed to rise to RT. The mixture is hydrolyzed by the addition of 250 ml of water; after decantation, the organic phase is washed with 10% HCl solution, with saturated NaCl solution and with water and dried over $MgSO_4$ and the solvent is evaporated off under vacuum. The residue is chromatographed on silica gel using toluene as the eluent to give 19.69 g of the expected product.

B/ 1-(2-(Morpholin-4-yl)ethyl)-2,7-dimethyl-3-(phenylthio)indole

A mixture of 2.4 g of the compound obtained in the previous step, 3 g of 4-(2-chloroethyl)morpholine, 2.23 g of finely ground KOH and 0.2 g of potassium iodide in 24 ml of DMSO is heated for 16 hours at 1 00° C. The reaction mixture is poured into 50 ml of water and extracted with toluene, the organic phase is washed with water and with saturated NaCl solution and dried over $MgSO_4$ and the solvent is evaporated off under vacuum. 0.7 g of the residue is chromatographed on silica gel using a toluene/AcOEt mixture (50/50; v/v) as the eluent to give 0.56 g of the expected product (m.p.=129.5° C.).

C/ 1-(2-(Morpholin-4-yl)ethyl)-2,7-dimethylindole

A mixture of 2.4 g of the compound obtained in the previous step and 2.2 g of 2-mercaptobenzoic acid in 24 ml of TFA is stirred for 3 hours at RT. The reaction mixture is concentrated under vacuum, the residue is taken up with an AcOEt/water mixture, the organic phase is washed with 10% NaOH solution, with water and with saturated NaCl solution and dried over $MgSO_4$ and the solvent is evaporated off under vacuum. The residue is chromatographed on silica gel using an AcOEt/toluene mixture (50/50; v/v) as the eluent to give 1.3 g of the expected product.

D/ 1-(2-(Morpholin-4-yl)ethyl)-2,7-dimethyl-3-(4-bromonaphth-1-ylcarbonyl)-indole A solution of 1.2 g of the compound obtained in the previous step and 1.68 g of 4-bromo-1-naphthoyl chloride in 50 ml of DCM is cooled to 0° C. under a nitrogen atmosphere, 5.7 ml of a 1.8 M solution of ethylaluminum dichloride in toluene are added and the reaction mixture is stirred for 36 hours at RT. It is poured into 100 ml of water and extracted with DCM, the organic phase is washed with 10% NaOH solution, with water and with saturated NaCl solution and dried over $MgSO_4$ and the solvent is evaporated off under vacuum. The residue is chromatographed on silica gel using an AcOEt/toluene mixture (70/30; v/v) as the eluent to give 0.36 g of the expected product (m.p.=143° C.).

TABLE 1

Compound of formula Ia ($R_{4a}$, $R_5$, $R_{7a}$ = H)

| No | $R_2$ | $R_8$ | $R_{3a}$ | M.p. (° C.) | COMPOUND DESCRIBED IN | SALT |
|---|---|---|---|---|---|---|
| 1 | H | naphth-1-yl | 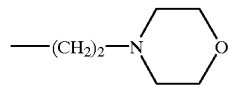 | 187 | EXAMPLE 6 | methanesulfonate |

TABLE 2

Compounds of formula Ib
($R_{1b}$ = —$CHR_9CH_2NR'_6R'_{11}$ where $R_9$ and $R_7$ together form a group —Y—$CH_2$—, Y being bonded to the 7-position of the indole)
($R_{4b}$ and $R_5$ = H)

| No | $R_2$ | $R_8$ | Y | Optical isomer | $NR'_6R'_{11}$ | M.p. (° C.) | Compound described in U.S. Pat. No. (Example) | Salt |
|---|---|---|---|---|---|---|---|---|
| 2 | $CH_3$ | naphth-1-yl | O | (+) | morpholin-4-yl (+) | 256–9 | US 5 109 135 (Ex 2B) | methanesulfonate |
| 3 | $CH_3$ | 4-bromonaphth-1-yl | O | (±) | morpholin-4-yl (±) | 281–6 | US 5 109 135 (Ex 2E) | methanesulfonate |
| 4 | $CH_3$ | 5,7-dibromonaphth-1-yl | O | (+) | morpholin-4-yl (+) | 256–7 | US 5 109 135 (Ex 1D) | methanesulfonate |
| 5 | $CH_3$ | naphth-1-yl | $CH_2$ | (+) | morpholin-4-yl (+) | 250 | EXAMPLE 5 | methanesulfonate |

TABLE 3

Compounds of formula Ib
($R_{1b}$ = $(CH_2)_2NR'_6R'_{11}$ or $CH_2CHR_{10}NR_6R_{11}$ or $(CH_2)_nZ$)
($R_{4b}$ and $R_5$ = H)

| No | $R_2$ | $R_8$ | $R_7$ | $R_{1b}$ | M.p. (° C.) | Compound described in U.S. Pat. No. (Example) |
|---|---|---|---|---|---|---|
| 6 | $CH_3$ | naphth-1-yl | $OCH_3$ | —$(CH_2)_2$—morpholin-4-yl | 225–7 | US 5 013 837 (Ex 2AO) |
| 7 | H | 4-bromonaphth-1-yl | H | —$(CH_2)_2$—morpholin-4-yl | 164–6 | US 5 013 837 (Ex 2AW) |
| 8 | H | naphth-1-yl | H | —$CH_2$—CH(N-Me)-piperidine | 134–6 | EP 444 451 (Ex 2P) |
| 9 | $CH_3$ | naphth-1-yl | H | —$CH_2$—CH(N-Me)-piperidine | 140–1 | EP 444 451 Ex 2R) |

TABLE 3-continued

Compounds of formula Ib
($R_{1b}$ = $(CH_2)_2NR'_6R'_{11}$ or $CH_2CHR_{10}NR_6R_{11}$ or $(CH_2)_nZ$)
($R_{4b}$ and $R_5$ = H)

| No | $R_2$ | $R_8$ | $R_7$ | $R_{1b}$ | M.p. (° C.) | Compound described in U.S. Pat. No. (Example) |
|---|---|---|---|---|---|---|
| 10 | $CH_3$ | naphth-1-yl | H | 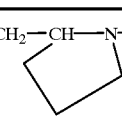 —$CH_2$—CH—N—$CH_3$ (cyclopentyl ring) | 110–2 | EP 444 451 (Ex 2Q) |
| 11 | $CH_3$ | 4-fluoronaphth-1-yl | $OCH_3$ | —$(CH_2)_2$—N(morpholine) | 175 | EXAMPLE 1 |
| 12 | $CH_3$ | 4-chloronaphth-1-yl | $OCH_3$ | —$(CH_2)_2$—N(morpholine) | 149 | EXAMPLE 2 |
| 13 | $CH_3$ | naphth-1-yl | H | $(CH_2)_3Br$ | 115–6 | EP 171 037 (Ex 7F) |
| 14 | $CH_3$ | 4-chloronaphth-1-yl | $OCH_3$ | $(CH_2)_4CH_3$ | 112 | EXAMPLE 3 |
| 15 | $CH_3$ | 4-methoxyphenyl | H | $(CH_2)_4Br$ | 83–6 | EP 171 037 (Ex 7E) |

TABLE 4

Compound of formula Ic
($R_{1c}$ is a group —$CHR_9CH_2NR'_6R'_{11}$ in which $R_9$ together with $R_7$ forms a group —Y—$CH_2$—
where Y is bonded to the 7-position of the indole ring)

| No | $R_2$ | $R_8$ | Y | $NR'_6R'_{11}$ | M.p. (° C.) | COMPOUND DESCRIBED IN | SALT | ISOMER |
|---|---|---|---|---|---|---|---|---|
| 16 | $CH_3$ | 5,7-dibromonaphth-1-yl | O | —N(morpholine) 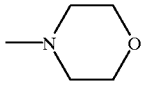 | 258 | EXAMPLE 4 | methanesulfonate | (–) |

TABLE 5

Compounds of formula (1')
($R'_3$ is a group =$CR_6R_8$ and $R'_1$ is a group —$(CH_2)_2NR'_6R'_{11}$)
($R'_5$ and $R_6$ = H)

| No | $R'_2$ | $R_8$ | $NR'_6R'_{11}$ | M.p. (° C.) | Compound described in U.S. Pat. No. (Example) | SALT |
|---|---|---|---|---|---|---|
| 17 | H | 4-$OCH_3$-naphth-1-yl | —N(morpholine) 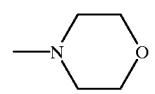 | 249–51 | US 5 292 736 (Ex 8) | — |
| 18 | $CH_3$ | naphth-1-yl | " | 282–4 | US 5 292 736 (Ex 10) | HCl |
| 19 | $CH_3$ | 4-$OCH_3$-naphth-1-yl | " | 265–7 | US 5 292 736 (Ex 16) | HCl |

TABLE 5-continued

Compounds of formula (1')
($R'_3$ is a group $=CR_6R_8$ and $R'_1$ is a group $-(CH_2)_2NR'_6R'_{11}$)
($R'_5$ and $R_6$ = H)

| No | $R'_2$ | $R_8$ | $NR'_6R'_{11}$ | M.p. (° C.) | Compound described in U.S. Pat. No. (Example) | SALT |
|----|--------|-------|----------------|-------------|----------------------------------------------|------|
| 20 | H | 4-OH-naphth-1-yl | " | 219–21 | US 5 292 736 (Ex 19) | HCl |
| 21 | H | 9-anthryl | " | 170–2 | US 5 292 736 (Ex 20) | — |

TABLE 6

Compounds of formula Ib
($R_{1b}$ = $(CH_2)_2NR'_6R'_{11}$ or $(CH_2)_nZ$)
($R_{4b}$ and $R_5$ = H)

| No | $R_2$ | $R_8$ | $R_7$ | $R_{1b}$ | M.p. (° C.) | Compound described in |
|----|-------|-------|-------|----------|-------------|----------------------|
| 22 | $CH_3$ | 4-bromonaphth-1-yl | $OCH_3$ | $-(CH_2)_2-N\langle morpholino\rangle$ | 123–5 | EXAMPLE 7 |
| 23 | $CH_3$ | 4-bromonaphth-1-yl | $OCH_3$ | $-(CH_2)_4CH_2$ | 114.5 | EXAMPLE 8 |
| 24 | $CH_3$ | naphth-1-yl | $CF_3$ | $-(CH_2)_2-N\langle morpholino\rangle$ | 104 | EXAMPLE 9 |
| 25 | $CH_3$ | 4-bromonaphth-1-yl | $CF_3$ | $-(CH_2)_2-N\langle morpholino\rangle$ | 160 | EXAMPLE 10 |
| 26 | $CH_3$ | 4-bromonaphth-1-yl | F | $-(CH_2)_2-N\langle morpholino\rangle$ | 66–7 | EXAMPLE 11 |
| 27 | $CH_3$ | 4-bromonaphth-1-yl | F | $-(CH_2)_4CH_2$ | — | EXAMPLE 12 |
| 28 | $CH_3$ | 4-bromonaphth-1-yl | $CH_3$ | $-(CH_2)_2-N\langle morpholino\rangle$ | 143 | EXAMPLE 13 |

BIOCHEMICAL TEST

It has been shown that, at nanomolar concentrations, compounds according to the invention, such as 3-(morpholin-4-ylmethyl)-5-methyl-6-(naphth-1-ylcarbonyl)-2,3-dihydropyrrolo[1,2,3-de]-1,4-benzoxazine methanesulfonate and 1-(2-(morpholin-4-yl)ethyl)-2-methyl-3-(naphth-1-ylcarbonyl)-7-methoxyindole, are capable of substantially increasing the DNA synthesis rate of human B cells co-stimulated with anti-Ig antibodies (increase of about 40% in the thymidine absorption).

When the selective $CB_1$ receptor antagonist SR 141716A was used over a wide concentration range at the same time as the compound CP 55940 (or $\Delta^9$-THC or WIN 55212-2) at $10^{-9}$ M, no blocking effect was observed.

The same phenomenon, i.e. an increase in the growth of B cells, could be observed using another activation route consisting in stimulating human B cells by bringing the CD 40 antigen into contact with monoclonal antibodies presented by L CD W32 cells.

The compounds (I) and (I') according to the invention and their salts, where appropriate, showed a 30 to 1000 times greater in vitro affinity for the peripheral human cannabinoid receptors (CB$_2$) than for the central human receptors (CB$_1$) expressed in Chinese hamster ovary (CHO) cells. Affinity binding tests were carried out under the experimental conditions described by Devane et al. (Molecular Pharmacology (1988) 34, 605–613) with membranes derived from cell lines in which the CB$_1$ and CB$_2$ receptors were expressed (Munro et al., Nature (1993) 365, 561–565).

The preferred compounds are as follows:

1-(2-(morpholin-4-yl)ethyl)-2-methyl-3-(naphth-1-ylcarbonyl)-7-methoxyindole;

1-(naphth1-ylcarbonyl)-3-(2-(morpholin-4-yl)ethyl)indole methanesulfonate;

2-methyl-1-[2-(1-methylpiperidin-2-yl)methyl]-3-(naphth-1-ylcarbonyl)indole;

(+)-(2-methyl-4-(morpholin-4-ylmethyl)-5,6-dihydro-4H-pyrrolo[3,2,1-ij]-quinolin-1-yl)naphthalen-1-ylmethanone methanesulfonate;

4-[2-[1-[(naphth-1-yl)methylene]1-methylinden-3-yl]ethyl] morpholine;

4-[2-[1-[1-(4-methoxynaphthyl)methylene]-1-methylinden-3-yl]ethyl]morpholine;

4-[2-[1-[(9-anthryl)methylene]-1H-inden-3-yl]ethyl] morpholine;

1-(2-(morpholin-4-yl)ethyl)-2-methyl-3-(4-bromonaphth-1-ylcarbonyl)-7-methoxyindole;

1-n-pentyl-2-methyl-3-(4-bromonaphth-1-ylcarbonyl)-7-methoxyindole;

1-(2-(morpholin-4-yl)ethyl)-2-methyl-3-(4-bromonaphth-1-ylcarbonyl)-7-(trifluoromethyl)indole; and 1-n-pentyl-2-methyl-3-(4-bromonaphth-1-ylcarbonyl)-7-fluoroindole.

A particularly preferred compound is 1-(2-(morpholin-4-yl)ethyl)-2-methyl-3-(4-bromonaphth-1-ylcarbonyl)-7-methoxyindole, whose affinity for the CB$_1$ receptor is greater than 1000 nM and for the CB$_2$ receptor is 1.8 nM.

Furthermore, the compounds according to the invention behave in vitro as specific agonists for the human CB$_2$ cannabinoid receptors relative to the CB$_1$ receptors expressed in CHO cells. In fact, by binding specifically to the CB$_2$ receptors, they reduce forskolin-stimulated cAMP production by inhibiting the adenylate cyclase. The tests were carried out under the experimental conditions described by Matsuda et al. (Nature, 1990, 346, 561–564).

By way of example, the following adenylate cyclase 50% inhibitory concentrations, IC$_{50}$, were calculated for 1-(2-(morpholin-4-yl)ethyl)-2-methyl-3-(4-bromonaphth-1-ylcarbonyl)-7-methoxyindole:

IC$_{50}$=1 nM in the case of CB$_2$

IC$_{50}$=1 μM in the case of CB$_1$.

The compounds according to the invention also possess an in vivo affinity for the cannabinoid receptors present in mouse spleen when they are administered intravenously, intraperitoneally or orally. The tests were carried out under the experimental conditions described by Rinaldi-Carmona et al. (Life Sciences, 1995, 56, 1941–1947).

What is claimed is:
1. Compounds of formula (Ib$_1$):

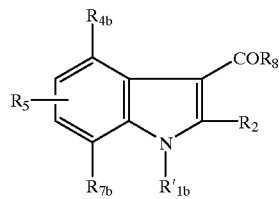

in which
R'$_{1b}$ is a group having a formula —CH$_2$CHR$_{10}$NR$_6$R$_{11}$ or —(CH$_2$)$_2$NR'$_6$R'$_{11}$;

R$_2$ is hydrogen, a halogen or a(C$_1$–C$_4$)alkyl;

R$_{4b}$ is hydrogen, a (C$_1$–C$_4$)alkyl, a (C$_1$–C$_4$)alkoxy, a halogen atom, a group —CF$_3$, a group —OCF$_3$ or a (C$_1$–C$_4$)alkylthio;

R$_5$ is hydrogen, a (C$_1$–C$_4$)alkyl, a (C$_1$–C$_4$)alkoxy, a halogen atom, a group CF$_3$, a group OCF$_3$ or a (C$_1$–C$_4$) alkylthio;

R$_6$ is hydrogen or a (C$_1$–C$_4$)alkyl;

R'$_6$ is a (C$_1$–C$_4$)alkyl;

R$_{7b}$ is a (C$_1$–C$_4$)alkyl, a (C$_1$–C$_4$)alkoxy, a halogen atom, a group —CF$_3$, a group —OCF$_3$ or a (C$_1$–C$_4$)alkylthio;

R$_8$ is a phenyl monosubstituted to tetrasubstituted by a substituent selected from the group consisting of a halogen atom, a (C$_1$–C$_4$)alkyl and a (C$_1$–C$_4$)alkoxy; or a polycyclic radical selected from a naphth-1-yl, a naphth-2-yl, a 1,2,3,4-tetrahydronaphth-1-yl, a 1,2,3,4-tetrahydronaphth-5-yl, an anthryl, a benzofuryl, a benzothien-2-yl, a benzothien-3-yl and a 2-, 3-, 4- or 8-quinolyl, said polycyclic radicals being unsubstituted or monosubstituted or disubstituted by a substituent selected from the group consisting of a (C$_1$–C$_4$)alkyl, a (C$_1$–C$_4$)alkoxy, a (C$_1$–C$_4$)alkylthio, a halogen, a cyano, a hydroxyl, a trifluoromethyl and an imidazol-1-yl;

R$_{10}$ and R$_{11}$ together are a group selected from the group consisting of —CH$_2$—O—CH$_2$—CR$_{12}$R$_{13}$— and —(CH$_2$)$_p$—CR$_{12}$R$_{13}$—, in which the carbon atom substituted by R$_{12}$ and R$_{13}$ is bonded to the nitrogen atom;

R'$_{11}$ is a (C$_1$–C$_4$)alkyl, or R'$_{11}$ and R'$_6$, together with the nitrogen atom to which they are bonded, form a group selected from the group consisting of morpholin-4-yl, thiomorpholin-4-yl, piperidin-1-yl and pyrrolidin-1-yl groups;

R$_{12}$ and R$_{13}$ independently of one another are each hydrogen or a (C$_1$–C$_4$)alkyl;

p is 2 or 3;

at least one of the groups R$_{4b}$, R$_5$ is hydrogen, or pharmaceutically acceptable salts thereof, with the proviso that;

1) if
   if R'$_{1b}$ is the group —CH$_2$CHR$_{10}$NR$_6$R$_{11}$;
   R$_2$ is hydrogen or a (C$_1$–C$_4$)alkyl group;
   R$_{4b}$ and R$_5$ are selected from a hydrogen, a (C$_1$–C$_4$) alkyl, a (C$_1$–C$_4$)alkoxy or a halogen atom,
   R$_{7b}$ is selected from a (C$_1$–C$_4$)alkyl, a (C$_1$–C$_4$)alkoxy or a halogen atom;
then R$_8$ is different from a phenyl group monosubstituted or disubstituted by a halogen, a (C$_1$–C$_4$) alkyl, a (C$_1$–C$_4$) alkoxy; from a 1- or 2-naphthyl group unsubstituted or monosubstituted or disubstituted by a $(C_1-C_4)$alkyl, a $(C_1-C_4)$alkoxy, a halogen or a $(C_1-C_4)$alkylthio;

2) if $R'_{1b}$ is the group $(CH_2)_2NR'_6R'_{11}$, then one of the groups $R_{4b}$, $R_5$, $R_{7b}$ is selected from —$CF_3$, $OCF_3$, or $(C_1-C_4)$alkylthio.

2. Compounds of formula $(Ib_2)$:

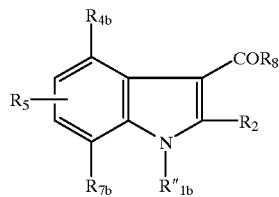

in which:

$R''_{1b}$ is a group —$(CH_2)_nZ$;

$R_2$ is hydrogen, a halogen atom or a $(C_1-C_4)$alkyl;

$R_{4b}$ is hydrogen, a $(C_1-C_4)$alkyl, a $(C_1-C_4)$alkoxy, a halogen atom, a group —$CF_3$, a group —$OCF_3$ or a $(C_1-C_4)$alkylthio;

$R_5$ is hydrogen, a $(C_1-C_4)$alkyl, a $(C_1-C_4)$alkoxy, a halogen atom, a group $CF_3$, a group $OCF_3$ or a $(C_1-C_4)$alkylthio;

$R_{7b}$ is a $(C_1-C_4)$alkyl, a $(C_1-C_4)$alkoxy, a halogen atom, a group —$CF_3$, a group —$OCF_3$ or a $(C_1-C_4)$alkylthio;

$R_8$ is a phenyl monosubstituted to tetrasubstituted by a substituent selected from the group consisting of a halogen atom, a $(C_1-C_4)$alkyl and a $(C_1-C_4)$alkoxy; or a polycyclic radical selected from a naphth-1-yl, a naphth-2-yl, a 1,2,3,4-tetrahydronaphth-1-yl, a 1,2,3,4-tetrahydronaphth-5-yl, an anthryl, a benzofuryl, a benzothien-2-yl, a benzothien-3-yl and a 2-, 3-, 4- or 8-quinolyl, said polycyclic radicals being unsubstituted or monosubstituted or disubstituted by a substituent selected from the group consisting of a $(C_1-C_4)$alkyl, a $(C_1-C_4)$alkoxy, a $(C_1-C_4)$alkylthio, a halogen, a cyano, a hydroxyl, a trifluoromethyl and an imidazol-1-yl;

n is 2, 3, 4, or 5;

Z is a methyl group or a halogen atom; and at least one of the groups $R_{4b}$, $R_5$ is hydrogen;

or a pharmaceutically acceptable salt thereof.

3. Compounds of formula $(Ib_3)$:

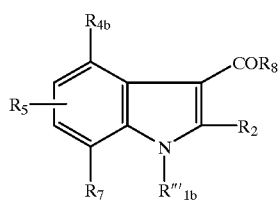

in which:

$R'''_{1b}$ is a group having a formula —$CHR_9CH_2NR'_6R'_{11}$;

$R_2$ is hydrogen, a halogen atom or a $(C_1-C_4)$alkyl;

$R_{4b}$ is hydrogen, a $(C_1-C_4)$alkyl, a $(C_1-C_4)$alkoxy, a halogen atom, a group —$CF_3$, a group —$OCF_3$ or a $(C_1-C_4)$alkylthio;

$R_5$ is hydrogen, a $(C_1-C_4)$alkyl, a $(C_1-C_4)$alkoxy, a halogen atom, a group $CF_3$, a group $OCF_3$ or a $(C_1-C_4)$alkylthio;

$R'_6$ is a $(C_1-C_4)$alkyl;

$R_7$ is a $(C_1-C_4)$alkyl, a $(C_1-C_4)$alkoxy, a halogen atom, a group —$CF_3$, a group —$OCF_3$ or a $(C_1-C_4)$alkylthio, or $R_7$ and $R_9$ together form a group —Y—$CH_2$— bonded to the indole ring in the 7-position by the group Y;

$R_8$ is a phenyl monosubstituted to tetrasubstituted by a substituent selected from a halogen, a $(C_1-C_4)$alkyl and a $(C_1-C_4)$alkoxy; or a polycyclic radical selected from the group consisting of a naphth-1-yl, a naphth-2-yl, a 1,2,3,4-tetrahydronaphth-1-yl, a 1,2,3,4-tetrahydronaphth-5-yl, an anthryl, a benzofuryl, a benzothien-2-yl, a benzothien-3-yl and a 2-, 3-, 4- or 8-quinolyl, said polycyclic radicals being unsubstituted or monosubstituted or disubstituted by a substituent selected from the group consisting of a $(C_1-C_4)$alkyl, a $(C_1-C_4)$alkoxy, a $(C_1-C_4)$alkylthio, a halogen atom, a cyano, a hydroxyl, a trifluoromethyl and an imidazol-1-yl;

$R'_{11}$ is a $(C_1-C_4)$alkyl, or $R'_{11}$ and $R'_6$, together with the nitrogen atom to which they are bonded, form a group selected from the group consisting of morpholin-4-yl, thiomorpholin-4-yl, piperidin-1-yl and pyrrolidin-1-yl groups;

at least one of the groups $R_{4b}$ and $R_5$ is hydrogen, or a pharmaceutically acceptable salt thereof, with the proviso that:

if $R_2$ is hydrogen or a $(C_1-C_4)$alkyl group;

Y is oxygen;

$R_{4b}$ is hydrogen, a $(C_1-C_4)$alkyl; a $(C_1-C_4)$alkoxy or a halogen;

$R_5$ is hydrogen, a $(C_1-C_4)$alkyl; a $(C_1-C_4)$alkoxy or a halogen;

then $R_8$ is different from a phenyl monosubstituted or disubstituted by a halogen, a $(C_1-C_4)$alkyl, a $(C_1-C_4)$alkoxy; from a 1- or 2-naphthyl group unsubstituted or monosubstituted or disubstituted by a substituent selected from a $(C_1-C_4)$alkyl, a $(C_1-C_4)$alkoxy, a $(C_1-C_4)$alkylthio, a hydroxy; from a 2-, 3-, 4- or 8-quinolyl.

4. A Compound which is selected from the group consisting of:

1-(2-(morpholin-4-yl)ethyl)-2-methyl-3-(4-fluoronaphth-1-ylcarbonyl)-7-methoxyindole;

1-(2-(morpholin-4-yl)ethyl)-2-methyl-3-(4-chloronaphth-1-ylcarbonyl)-7-methoxyindole;

1-n-pentyl-2-methyl-3-(4-chloronaphth-1-ylcarbonyl)-7-methoxyindole;

1-(2-(morpholin-4-yl)ethyl)-2-methyl-3-(4-bromonaphth-1-ylcarbonyl)-7-methoxyindole;

1-n-pentyl-2-methyl-3-(4-bromonaphth-1-ylcarbonyl)-7-methoxyindole;

1-(2-(morpholin-4-yl)ethyl)-2-methyl-3-(naphth-1-ylcarbonyl)-7-(trifluoromethyl)indole;

1-(2-(morpholin-4-yl)ethyl)-2-methyl-3-(4-bromonaphth-1-ylcarbonyl)-7-(trifluoromethyl)indole;

1-(2-(morpholin-4-yl)ethyl)-2-methyl-3-(4-bromonaphth-1-ylcarbonyl)-7-fluoroindole;

1-n-pentyl-2-methyl-3-(4-bromonaphth-1-ylcarbonyl)-7-fluoroindole; and 1-(2-(morpholin-4-yl)ethyl)-2,7-dimethyl-3-(4-bromonaphth-1-ylcarbonyl)indole.

5. A pharmaceutical composition containing a compound of claim 1, or one of its pharmaceutically acceptable salts, as the active principle, and a pharmaceutical vehicle.

6. A pharmaceutical composition containing a compound of claim 2, or one of its pharmaceutically acceptable salts, as the active principle, and a pharmaceutical vehicle.

7. A pharmaceutical composition containing a compound of claim 3, or one of its pharmaceutically acceptable salts, as the active principle, and a pharmaceutical vehicle.

8. A pharmaceutical composition containing a compound of claim 4, or one of its pharmaceutically acceptable salts, as the active principle, and a pharmaceutical vehicle.

* * * * *